United States Patent
Wakamiya et al.

(10) Patent No.: US 8,871,147 B2
(45) Date of Patent: Oct. 28, 2014

(54) SAMPLE ANALYZER AND STORAGE MEDIUM

(75) Inventors: Yuji Wakamiya, Kobe (JP); Tomohiro Okuzaki, Himeji (JP)

(73) Assignee: Sysmex Corporation (JP)

( * ) Notice: Subject to any disclaimer, the term of this patent is extended or adjusted under 35 U.S.C. 154(b) by 102 days.

(21) Appl. No.: 13/455,935

(22) Filed: Apr. 25, 2012

(65) Prior Publication Data

US 2012/0275956 A1    Nov. 1, 2012

(30) Foreign Application Priority Data

Apr. 28, 2011  (JP) .................................. 2011-102235
Sep. 30, 2011  (JP) .................................. 2011-217129

(51) Int. Cl.
*G01N 1/10*    (2006.01)
*G01N 33/18*   (2006.01)
*G01N 35/00*   (2006.01)

(52) U.S. Cl.
CPC .. *G01N 33/1826* (2013.01); *G01N 2035/00673* (2013.01); *G01N 33/18* (2013.01); *G01N 2035/00891* (2013.01); *G01N 35/00663* (2013.01)
USPC ................. 422/67; 702/22; 422/68.1; 422/64

(58) Field of Classification Search
CPC .......... G01N 2035/00673; G01N 2035/00891; G01N 35/00663
See application file for complete search history.

(56) References Cited

U.S. PATENT DOCUMENTS

| | | | |
|---|---|---|---|
| 6,090,630 A | 7/2000 | Koakutsu et al. | |
| 2008/0279048 A1* | 11/2008 | Wakamiya et al. | 368/10 |
| 2010/0114501 A1* | 5/2010 | Kondou et al. | 702/22 |

FOREIGN PATENT DOCUMENTS

| | | | |
|---|---|---|---|
| JP | 05-164760 | * | 6/1993 |
| JP | 05-164760 A | | 6/1993 |
| JP | 2003-315344 | * | 11/2003 |
| JP | 2003-315344 A | | 11/2003 |

* cited by examiner

*Primary Examiner* — Kathryn Wright
(74) *Attorney, Agent, or Firm* — Brinks Gilson & Lione

(57) ABSTRACT

A sample analyzer comprising: a measurement unit holds a reagent to be used in a sample measurement and measures a sample by using the reagent; a memory storing a usage amount of the reagent used by the measurement unit; a controller calculates an estimated usage amount of the reagent for a specific day, based on the usage amount of the reagent stored in the memory; and a display, wherein the controller controls the display to show a screen including graphic information illustrating a remaining amount of the reagent held by the measurement unit and the estimated usage amount of the reagent for the specific day, first numerical information indicating, by means of a numerical value, the remaining amount of the reagent, and second numerical information indicating an excess or shortage amount of the remaining amount of the reagent relative to the estimated usage amount of the reagent.

12 Claims, 24 Drawing Sheets

FIG. 10

| MONDAY | | TUESDAY | | WEDNESDAY | | THURSDAY | | FRIDAY | | SATURDAY | | SUNDAY | |
|---|---|---|---|---|---|---|---|---|---|---|---|---|---|
| 9/27 | 200 | 9/28 | 160 | 9/29 | 153 | 9/30 | 164 | 10/1 | 182 | 10/2 | 0 | 10/3 | 0 |
| 10/4 | 209 | 10/5 | 5 | 10/6 | 187 | 10/7 | 161 | 10/8 | 179 | 10/9 | 0 | 10/10 | 0 |
| 10/11 | 23 | 10/12 | 210 | 10/13 | 162 | 10/14 | 165 | 10/15 | 173 | 10/16 | 0 | 10/17 | 0 |
| 10/18 | 21 | 10/19 | 34 | 10/20 | 190 | 10/21 | 170 | 10/22 | 180 | 10/23 | 0 | 10/24 | 0 |
| 10/25 | 209 | 10/26 | 170 | 10/27 | 154 | 10/28 | 162 | 10/29 | 182 | 10/30 | 0 | 10/31 | 0 |
| 11/1 | 211 | 11/2 | 181 | 11/3 | 5 | 11/4 | 161 | 11/5 | 179 | 11/6 | 0 | 11/7 | 0 |
| 11/8 | 201 | 11/9 | 178 | 11/10 | 152 | 11/11 | 162 | 11/12 | 181 | 11/13 | 0 | 11/14 | 0 |
| 11/15 | 310 | 11/16 | 175 | 11/17 | 152 | 11/18 | 169 | 11/19 | 176 | 11/20 | 0 | 11/21 | 0 |
| 11/22 | 209 | 11/23 | 4 | 11/24 | 6 | 11/25 | 221 | 11/26 | 187 | 11/27 | 0 | 11/28 | 0 |
| 11/29 | 203 | 11/30 | 169 | 12/1 | 150 | 12/2 | 168 | 12/3 | 186 | 12/4 | 0 | 12/5 | 0 |
| 12/6 | 241 | 12/7 | 170 | 12/8 | 154 | 12/9 | 162 | 12/10 | 182 | 12/11 | 0 | 12/12 | 0 |
| 12/13 | 20 | 12/14 | 179 | 12/15 | 151 | 12/16 | 167 | 12/17 | 200 | 12/18 | 0 | 12/19 | 0 |
| 12/20 | 201 | 12/21 | 168 | 12/22 | 153 | 12/23 | 21 | 12/24 | 188 | 12/25 | 0 | 12/26 | 0 |
| 12/27 | 206 | 12/28 | 6 | 12/29 | 187 | 12/30 | 0 | 12/31 | 0 | 1/1 | 0 | 1/2 | 0 |

| MONDAY | | TUESDAY | | WEDNESDAY | | THURSDAY | | FRIDAY | | SATURDAY | | SUNDAY | |
|---|---|---|---|---|---|---|---|---|---|---|---|---|---|
| 9/27 | 0 | 9/28 | 0 | 9/29 | 0 | 9/30 | 0 | 10/1 | 0 | 10/2 | 1 | 10/3 | 1 |
| 10/4 | 0 | 10/5 | 1 | 10/6 | 0 | 10/7 | 0 | 10/8 | 0 | 10/9 | 1 | 10/10 | 1 |
| 10/11 | 1 | 10/12 | 0 | 10/13 | 0 | 10/14 | 0 | 10/15 | 0 | 10/16 | 1 | 10/17 | 1 |
| 10/18 | 1 | 10/19 | 1 | 10/20 | 0 | 10/21 | 0 | 10/22 | 0 | 10/23 | 1 | 10/24 | 1 |
| 10/25 | 0 | 10/26 | 0 | 10/27 | 0 | 10/28 | 0 | 10/29 | 0 | 10/30 | 1 | 10/31 | 1 |
| 11/1 | 0 | 11/2 | 0 | 11/3 | 1 | 11/4 | 0 | 11/5 | 0 | 11/6 | 1 | 11/7 | 1 |
| 11/8 | 0 | 11/9 | 0 | 11/10 | 0 | 11/11 | 0 | 11/12 | 0 | 11/13 | 1 | 11/14 | 1 |
| 11/15 | 0 | 11/16 | 1 | 11/17 | 0 | 11/18 | 0 | 11/19 | 0 | 11/20 | 1 | 11/21 | 1 |
| 11/22 | 0 | 11/23 | 1 | 11/24 | 0 | 11/25 | 0 | 11/26 | 0 | 11/27 | 1 | 11/28 | 1 |
| 11/29 | 0 | 11/30 | 0 | 12/1 | 0 | 12/2 | 0 | 12/3 | 0 | 12/4 | 1 | 12/5 | 1 |
| 12/6 | 0 | 12/7 | 0 | 12/8 | 0 | 12/9 | 0 | 12/10 | 0 | 12/11 | 1 | 12/12 | 1 |
| 12/13 | 1 | 12/14 | 1 | 12/15 | 0 | 12/16 | 0 | 12/17 | 0 | 12/18 | 1 | 12/19 | 1 |
| 12/20 | 0 | 12/21 | 0 | 12/22 | 0 | 12/23 | 1 | 12/24 | 0 | 12/25 | 1 | 12/26 | 1 |
| 12/27 | 0 | 12/28 | 0 | 12/29 | 0 | 12/30 | 1 | 12/31 | 1 | 1/1 | 1 | 1/2 | 1 |

OPT

FIG. 23

| MEASUREMENT ITEM | SET CONDITION | 2010/05/28 |
|---|---|---|
| HBsAg | 250 | +50 |
| HBsAb | 60 | -40 |
| TSH | 110 | +10 |
| FT3 | 0 | -100 |
| FT4 | 130 | +150 |
| TestA | 0 | -10 |
| TestB | 110 | +10 |
| TestC | 250 | +50 |
| TestD | 250 | +50 |
| TestE | 250 | +50 |
| TestF | 250 | |
| DILUENT | 250 | +50 |

☐ CONSUMABLE
CUVETTE
TIP

☐ To Do  2010/05/28  9:12
✓ CONFIRM REMAINING AMOUNT OF who1
  REAGENT AND REFILL
  SHUTDOWN  (18:30)

☐ BULLETIN BOARD
⊙ HISCL CLEANING SOLUTION WAS ORDERED
◇ SETTING WAS CHANGED

SAMPLE ANALYZER AND STORAGE MEDIUM

RELATED APPLICATIONS

This application claims priority under 35 U.S.C. §119 to Japanese Patent Application Nos. 2011-102235 filed on Apr. 28, 2011 and 2011-217129 filed on Sep. 30, 2011, the entire contents of which are hereby incorporated by reference.

BACKGROUND OF THE INVENTION

1. Field of the Invention

The present invention relates to a sample analyzer that analyzes samples using consumables such as reagents, and a storage medium for controlling a computer to display information of remaining amounts of consumables.

2. Description of the Related Art

Sample analyzers that automatically analyze samples such as blood, urine, and the like by using reagents have been known to date (for example, Japanese Laid-open Patent Publication No. 2003-315344, and Japanese Laid-open Patent Publication No. H5-164760). With such sample analyzers, unless a user discerns a shortage of a reagent before sample analyses are suspended due to depletion of the reagent, sample analyses cannot be effectively performed because sample analyses are suspended every time a reagent runs out.

Japanese Laid-open Patent Publication No. 2003-315344 discloses an analyzer that displays, by means of characters, a remaining amount of a reagent mounted in the apparatus and an estimated usage amount of the reagent calculated based on past analytical information. Specifically, an estimated number of analyses to be performed is calculated for each day of the week based on information of a past period, and an excess or shortage is estimated based on the remaining amount of the reagent mounted in the apparatus and on the calculated estimated number of analyses. Thus, the remaining amount of the reagent, the estimated number of analyses, and the estimated number of excesses or shortages are displayed on a screen in the form of character information.

Japanese Laid-open Patent Publication No. H5-164760 discloses an automatic analyzer that determines the number of samples to be measured for each measurement item based on an inputted measurement order, and calculates a necessary amount of a reagent, based on a usage amount of the reagent per measurement, which has been provided in advance, and on the number of samples to be measured. Moreover, Japanese Laid-open Patent Publication No. H5-164760 describes displaying vertically-extending bar graphs indicating the number of samples to be measured, a necessary amount of a reagent, a remaining amount of the reagent in a bottle, a shortage amount of the reagent, respectively.

However, in the analyzer disclosed in Japanese Laid-open Patent Publication No. 2003-315344, the remaining amount of a reagent, the estimated number of analyses, and the number of excesses and shortages are displayed only by characters. Therefore, it is difficult for the user to intuitively discern the necessary refill amount of the reagent. Moreover, the automatic analyzer disclosed in Japanese Laid-open Patent Publication No. H5-164760 calculates only an amount of a reagent necessary for processing a measurement order received at the current time. Therefore, the automatic analyzer cannot present to the user an amount of the reagent necessary for sample measurements to be performed, for example, for one day.

SUMMARY OF THE INVENTION

The scope of the present invention is defined solely by the appended claims, and is not affected to any degree by the statements within this summary.

A first aspect of the present invention is a sample analyzer comprising: a measurement unit capable of holding a reagent to be used in a sample measurement and configured to measure a sample by using the reagent; a memory configured to store a usage amount of the reagent which was used by the measurement unit; a controller configured to calculate an estimated usage amount of the reagent for a specific day, based on the usage amount of the reagent stored in the memory; and a display unit, wherein the controller is configured to control the display unit to show a screen image including graphic information graphically illustrating a remaining amount of the reagent held by the measurement unit and the estimated usage amount of the reagent for the specific day, first numerical information indicating, by means of a numerical value, the remaining amount of the reagent, and second numerical information indicating, by means of a numerical value, an excess or shortage amount of the remaining amount of the reagent relative to the estimated usage amount of the reagent.

A second aspect of the present invention is a sample analyzer comprising: a measurement unit capable of holding a reagent to be used in a sample measurement and configured to measure a sample by using the reagent; a memory configured to store a usage amount of the reagent which was used by the measurement unit; a controller configured to calculate an estimated usage amount of the reagent for a specific day, based on the usage amount of the reagent stored in the memory; and a display unit, wherein the controller is configured to control the display unit to show a screen image including a first bar graph indicating a remaining amount of the reagent held by the measurement unit and a second bar graph indicating the estimated usage amount of the reagent for the specific day, such that the first bar graph and the second bar graph are arranged in parallel to and adjacent to each other, with a width of the second bar graph being smaller than a width of the first bar graph.

A third aspect of the present invention is a sample analyzer comprising: a measurement unit capable of holding a reagent to be used in a sample measurement and configured to measure a sample by using the reagent; a memory configured to store a usage amount of the reagent which was used by the measurement unit; a controller configured to calculate an estimated usage amount of the reagent for a specific day, based on the usage amount of the reagent stored in the memory; and a display unit, wherein the controller is configured to control the display unit to show a screen image including a first bar graph indicating a remaining amount of the reagent held by the measurement unit and a second bar graph indicating the estimated usage amount of the reagent for the specific day, such that the first bar graph and the second bar graph are arranged in parallel with each other and the first bar graph overlaps the second bar graph, with the width of the second bar graph being greater than the width of the first bar graph.

A forth aspect of the present invention is a sample analyzer comprising: a measurement unit capable of holding a reagent to be used in a sample measurement and configured to measure a sample by using the reagent; a memory configured to store a usage amount of the reagent which was used by the measurement unit; a controller configured to calculate an estimated shortage amount of the reagent for a specific day, based on a past usage amount of the reagent stored in the memory and a remaining amount of the reagent held by the measurement unit; and a display unit, wherein the controller is configured to control the display unit to show a screen image including a first bar graph indicating the remaining amount of the reagent held by the measurement unit and a second bar graph indicating an estimated shortage amount of the reagent for the specific day, such that the first bar graph and the second bar graph in parallel with each other, with the second bar graph connected to an end of the first bar graph.

A fifth aspect of the present invention is a non-transitory storage medium having stored therein a computer-executable program executed by at least one processor of a computer system to: read out a usage amount of a reagent which was used by a measurement unit, from a memory; calculate an estimated usage amount of the reagent for a specific day, based on the usage amount of the reagent read out from the memory; and control a display unit to show a screen image including graphic information graphically illustrating a remaining amount of the reagent held by a measurement unit and the estimated usage amount of the reagent for the specific day, first numerical information indicating, by means of a numerical value, the remaining amount of the reagent, and second numerical information indicating, by means of a numerical value, an excess or shortage amount of the remaining amount of the reagent relative to the estimated usage amount of the reagent.

A sixth aspect of the present invention is a sample analyzer comprising: a measurement unit capable of holding a consumable to be used in a sample measurement and configured to measure a sample by using the consumable; a memory configured to store a usage amount of the consumable which was used by the measurement unit; a controller configured to calculate an estimated usage amount of the consumable for a specific day, based on the usage amount of the consumable stored in the memory; and a display unit, wherein the controller is configured to control the display unit to show a screen image including graphic information graphically illustrating a remaining amount of the consumable held by the measurement unit and the estimated usage amount of the consumable for the specific day, first numerical information indicating, by means of a numerical value, the remaining amount of the consumable, and second numerical information indicating, by means of a numerical value, an excess or shortage amount of the remaining amount of the consumable relative to the estimated usage amount of the consumable.

BRIEF DESCRIPTION OF THE DRAWINGS

FIG. 10 is a schematic diagram showing a structure of a reagent usage history database;

FIG. 13 is a schematic diagram showing a structure of an operation day table;

FIG. 23 is a diagram showing an example of a maintenance status confirmation screen;

DETAILED DESCRIPTION OF THE PREFERRED EMBODIMENTS

The preferred embodiments of the present invention will be described hereinafter with reference to the drawings.

[Structure of Sample Analyzer]

A sample analyzer according to the present embodiment is an immune analyzer that performs tests for various items such as hepatitis B, hepatitis C, tumor marker, and thyroid hormone, using a sample such as blood. In the sample analyzer according to the present embodiment, a capture antibody (R1 reagent) bound to an antigen contained in a measurement sample, such as blood, is bound to magnetic particles (R2 reagent), and the antigen, the capture antibody, and the magnetic particles which have been bound, are attracted to a magnet of a primary BF (bound free) separator 11 (see FIG. 1 and FIG. 2). Accordingly, the R1 reagent containing the capture antibody that is unreacted (free) is removed. Then, the antigen bound to the magnetic particles is bound to a labeled antibody (R3 reagent). Thereafter, the magnetic particles, the antigen, and the labeled antibody, which have been bound, are attracted to a magnet of a secondary BF separator 12. Accordingly, the R3 reagent containing the labeled antibody that is unreacted (free) is removed. Further, a dispersion liquid (R4 reagent) and a luminescent substrate (R5 reagent) which emits light in a reaction process with the labeled antibody are added. Thereafter, the amount of light generated by the reaction of the labeled antibody and the luminescent substrate is measured. Through this process, the amount of the antigen contained in the sample, which is bound to the labeled antibody, is measured.

Figure 1:
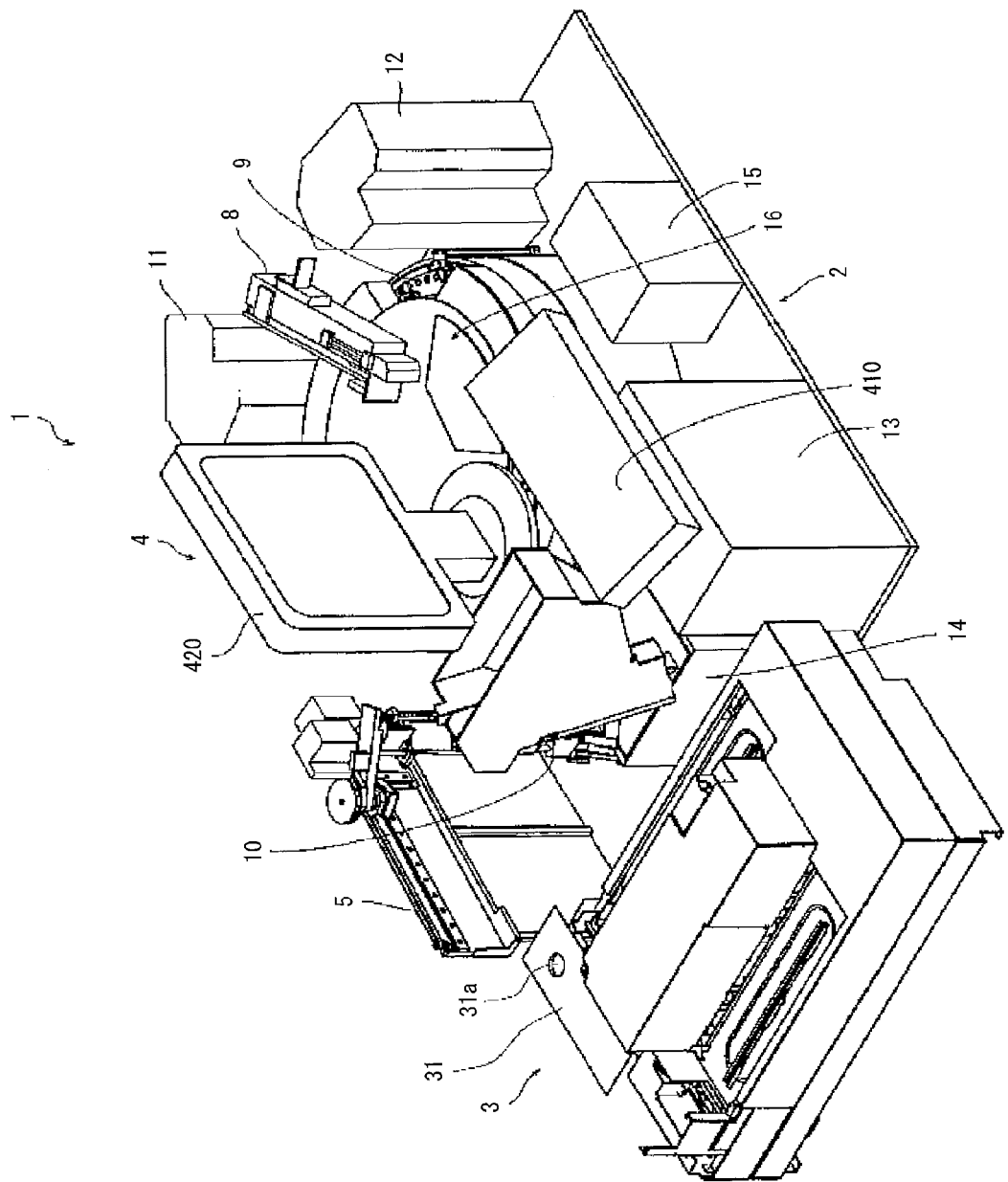
FIG. 1 is a perspective view showing a structure of a sample analyzer according to an embodiment.

FIG. 1 is a perspective view showing an overall structure of a sample analyzer 1.

The sample analyzer 1 according to the present embodiment includes a measurement mechanism unit 2, a sample transporting unit (sampler) 3 arranged adjacent to the measurement mechanism unit 2, and an information processing apparatus 4 electrically connected to the measurement mechanism unit 2.

The sample transporting unit 3 is configured to transport a rack in which a plurality of test tubes are set, each test tube containing a sample. The information processing apparatus 4 includes a body 400 (see FIG. 5), an input unit 410, and a display unit 420.

Figure 2:
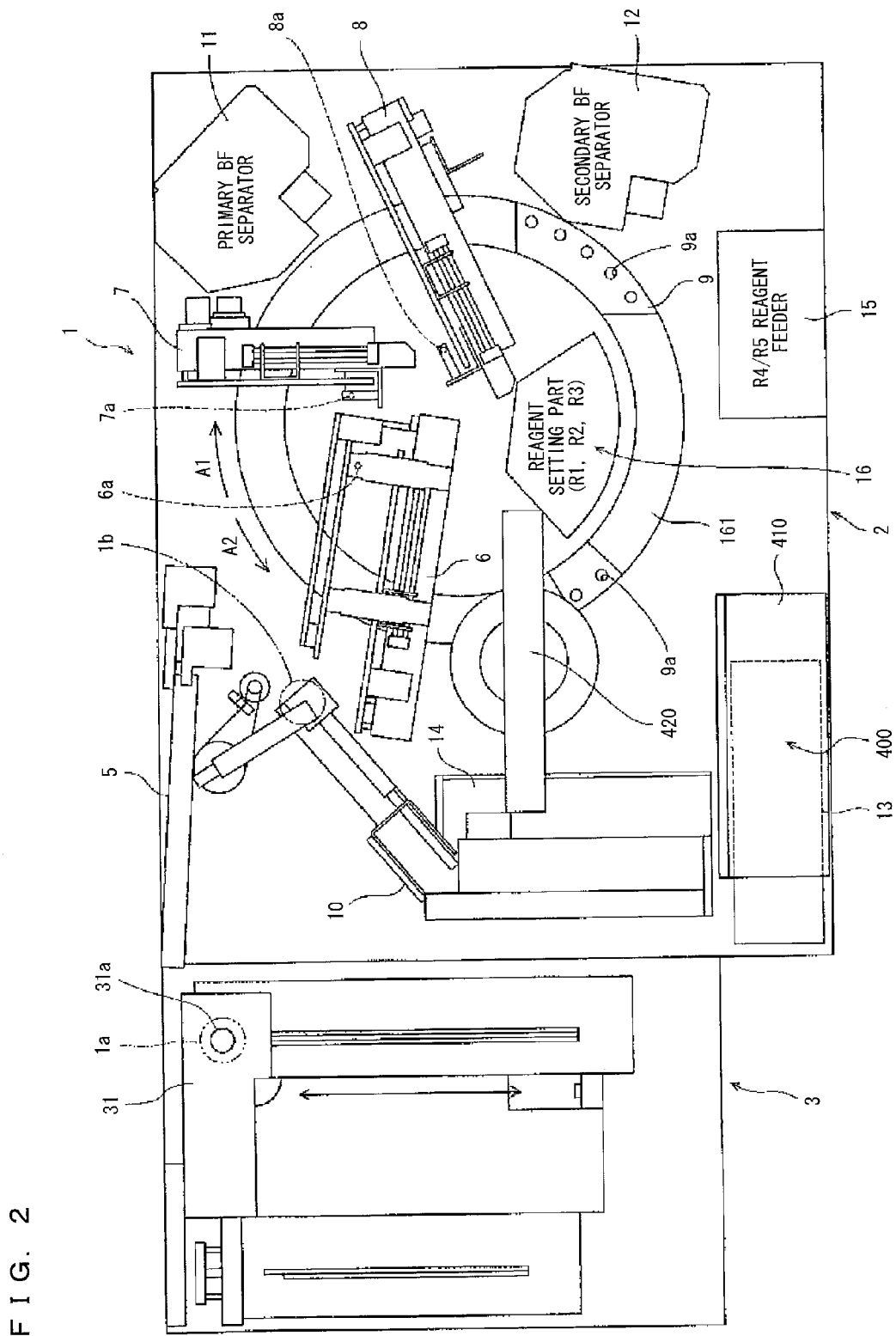
FIG. 2 is a schematic plan view showing a structure of a measurement mechanism unit included in a sample analyzer according to an embodiment.

FIG. 2 is a plan view showing a structure of the measurement mechanism unit 2, seen from above.

The measurement mechanism unit 2 includes a sample dispensing arm 5, an R1 reagent dispensing arm 6, an R2 reagent dispensing arm 7, an R3 reagent dispensing arm 8, a reaction part 9, a cuvette feeder 10, a primary BF separator 11, the secondary BF separator 12, a pipette tip feeder 13, a detector 14, an R4/R5 reagent feeder 15, and a reagent setting part 16.

The cuvette feeder 10 is configured to accommodate a plurality of cuvettes, and sequentially feeds cuvettes one by one to a sample discharging position 1b at which the sample dispensing arm 5 performs a sample discharging operation.

As shown in FIG. 2, a pipette 6a for aspirating and discharging the R1 reagent is attached to the R1 reagent dispensing arm 6. The R1 reagent dispensing arm 6 aspirates the R1 reagent set in the reagent setting part 16, using the pipette 6a, and dispenses the aspirated R1 reagent into a cuvette set at the sample discharging position 1b.

The pipette tip feeder 13 can accommodate a plurality of pipette tips. The pipette tip feeder 13 transports the fed plurality of pipette tips one by one to a tip attaching position at which a pipette tip is attached to the sample dispensing arm 5. At the tip attaching position, the pipette tip is attached to the end of the pipette of the sample dispensing arm 5.

After the pipette tip is attached to the pipette at the tip attaching position, the sample dispensing arm 5 aspirates, through a hole 31a formed in a top plate 31 covering a transporting path of the sample transporting unit 3, a sample from a test tube that has been transported to a sample aspirating position 1a by the sample transporting unit 3, and dispenses (discharges) the sample into the cuvette at the sample discharging position 1b into which the R1 reagent has been dispensed by the R1 reagent dispensing arm 6. Then, the cuvette is transported to the reaction part 9 by a catcher (not shown) of the R1 reagent dispensing arm 6.

As shown in FIG. 2, a pipette 7a for aspirating and discharging the R2 reagent is attached to the R2 reagent dispensing arm 7. The R2 reagent dispensing arm 7 aspirates, by means of the pipette 7a, the R2 reagent set in the reagent setting part 16, and dispenses (discharges) the aspirated R2 reagent into the cuvette containing the R1 reagent and the sample.

As shown in FIG. 2, the reaction part 9 is formed in an annular shape so as to surround the reagent setting part 16 which has a round shape. The reaction part 9 includes a plurality of cuvette setting parts 9a which are arranged along the outline of the reaction part 9 with predetermined intervals. Each cuvette setting part 9a is formed as a round U-shaped recess so as to allow a cuvette to be inserted therein, and has a function of heating the cuvette set therein to an approximately 42° C. Therefore, the specimen contained in the cuvette is heated to approximately 42° C. in the cuvette setting part 9a, whereby reaction between the sample and the various reagents in the cuvette is promoted. The reaction part 9 is configured to rotate in the clockwise direction (the arrow A1 direction), whereby the cuvettes set in the cuvette setting parts 9a are moved to positions at which various processes (such as reagent dispensing) are performed.

When a cuvette that contains the sample, the R1 reagent, and the R2 reagent is transferred by a catcher (not shown) from the reaction part 9 to the primary BF separator 11, the primary BF separator 11 separates (i.e., B/F separation) the R1 reagent that is unreacted (an unnecessary component) from magnetic particles in the specimen in the cuvette.

As shown in FIG. 2, a pipette 8a for aspirating and discharging the R3 reagent is attached to the R3 reagent dispensing arm 8. By means of the pipette 8a, the R3 reagent dispensing arm 8 aspirates the R3 reagent set in the reagent setting part 16. The R3 reagent dispensing arm 8 dispenses (discharges), by means of the pipette 8a, the aspirated R3 reagent to the cuvette that has been transferred from the primary BF separator 11 to the reaction part 9.

When the cuvette containing the R3 reagent and the specimen which has been subjected to the B/F separation by the primary BF separator 11 is transferred, by means of a catcher (not shown), from the reaction part 9 to the secondary BF separator 12, the secondary BF separator 12 separates (i.e., B/F separation) the R3 reagent that is unreacted (an unnecessary component) from magnetic particles in the specimen in the cuvette.

The R4/R5 reagent feeder 15 dispenses, by means of a tube not shown, the R4 reagent and the R5 reagent sequentially into the cuvette containing the specimen which has been subjected to the B/F separation by the secondary BF separator 12.

The detector 14 obtains, by means of a photo multiplier tube, light that is generated in a reaction between the luminescent substrate and the labeled antibody bound to an antigen in the sample on which the above-described predetermined processes have been performed, thereby measuring the amount of the antigen contained in the sample.

A cover 161 having a round shape is provided above the reagent setting part 16 so as to cover both the reagent setting part 16 and the reaction part 9. The cover 161 has openings formed at predetermined positions through which the R1 to R3 reagent dispensing arms aspirate reagents, move cuvettes, and dispense reagents.

Figure 3:
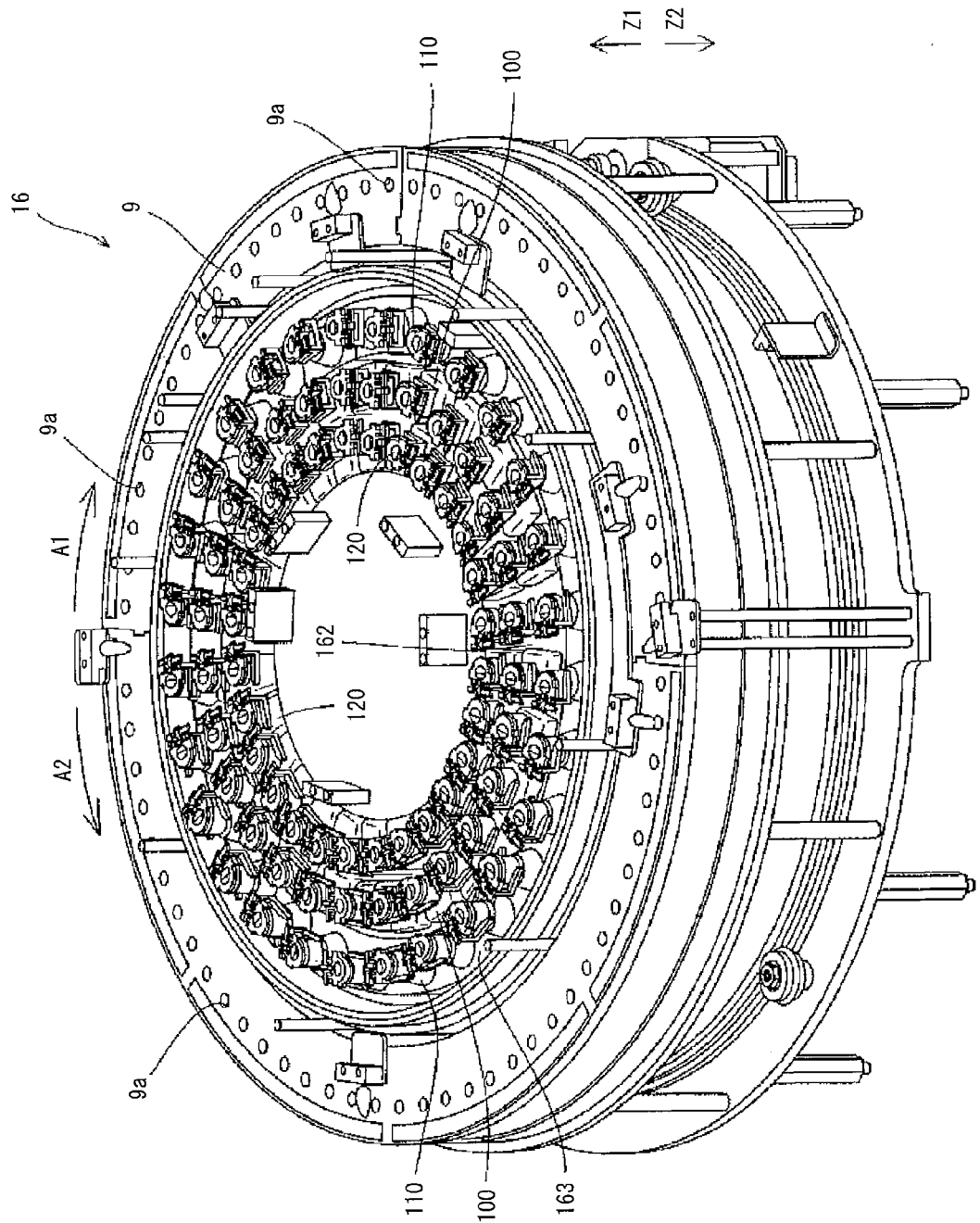
FIG. 3 is a perspective view showing a structure of a reagent setting part shown in FIG. 2.

FIG. 3 is a perspective view of the reagent setting part 16 without the cover 161. Seen from above, the reagent setting part 16 includes an inner table 162 and an outer table 163 both having annular shapes.

The inner table 162 includes a plurality of holders configured to hold R1 reagent containers 100 each for containing the R1 reagent, and a plurality of holders configured to hold R3 reagent containers 120 each for containing the R3 reagent. As shown in FIG. 3, these holders hold, on the inner table 162, the R1 reagent containers 100 in an annular manner so as to surround the R3 reagent containers 120 which are also arranged in an annular manner. As described below, the R1 reagent containers 100 held on the inner table 162 are arranged such that they are adjacent, in a radial direction, to the R3 reagent containers 120, respectively.

The inner table 162 is configured to be horizontally rotatable in the clockwise direction (the arrow A1 direction) and in the anticlockwise direction (the arrow A2 direction). Specifically, the inner table 162 is configured to rotate by means of a first stepping motor 162a (see FIG. 4). When the inner table 162 rotates, the R1 reagent containers 100 and the R3 reagent containers 120 rotate in the same direction by the same angle.

The outer table 163 includes a plurality of holders configured to hold R2 reagent containers 110 each for containing the R2 reagent. As shown in FIG. 3, these holders hold, on the outer table 163, the R2 reagent containers 110 in an annular manner so as to surround R1 reagent containers 100 which are also arranged in an annular manner.

The outer table 163 is configured to be horizontally rotatable in the clockwise direction (the arrow A1 direction) and in the anticlockwise direction (the arrow A2 direction). Specifically, the outer table 163 is configured to rotate by means of a second stepping motor 163a (see FIG. 4). The outer table 163 is rotatable independently of the inner table 162. The outer table 163 has a function of rotating while agitating the R2 reagent contained in each R2 reagent container 110 held by the outer table 163.

An RFID tag is affixed to each reagent container set on the reagent setting part 16. Reagent management information for managing the reagent is stored in the RFID tag. The reagent management information contains information such as a measurement item, a lot number, a serial number, a reagent type, a preservation period, a filling amount, and a remaining amount.

The measurement item refers to a measurement item for which a measurement is performed by using the reagent contained in the reagent container to which the RFID tag is affixed. R1/R3 reagent containers and R2 reagent containers 110 are each uniquely identified by its measurement item, lot number, and serial number. The serial number is a number that allows the corresponding reagent container to be uniquely identified among other reagent containers for which the same measurement item and the same lot number are set. An R1/R3 reagent container and an R2 reagent container 110 that share the same measurement item and the same lot number are packed together and provided to the user. Due to the nature of usage of R1/R3 reagent containers and R2 reagent containers 110, each R1/R3 reagent container is used in combination with (i.e., paired with) an R2 reagent container 110 having the same measurement item and the same lot number as those of the R1/R3 reagent container.

The reagent type indicates whether the reagent container to which the RFID tag is affixed is an R1/R3 reagent container or an R2 reagent container 110. The preservation period indicates until when the reagent can be preserved. The filling amount indicates the number of tests (the number of times of measurements) that can be performed by using this reagent. The remaining amount indicates a remaining number of tests (a remaining number of times of measurements) that can be performed by using this reagent. An expiration date indicates until when the reagent can be used. The expiration date is set when the reagent is started to be used.

The reagent setting part 16 is provided with antennas 162b and 163b (see FIG. 4) for reading and writing the reagent management information stored in the RFID tag.

Figure 4:
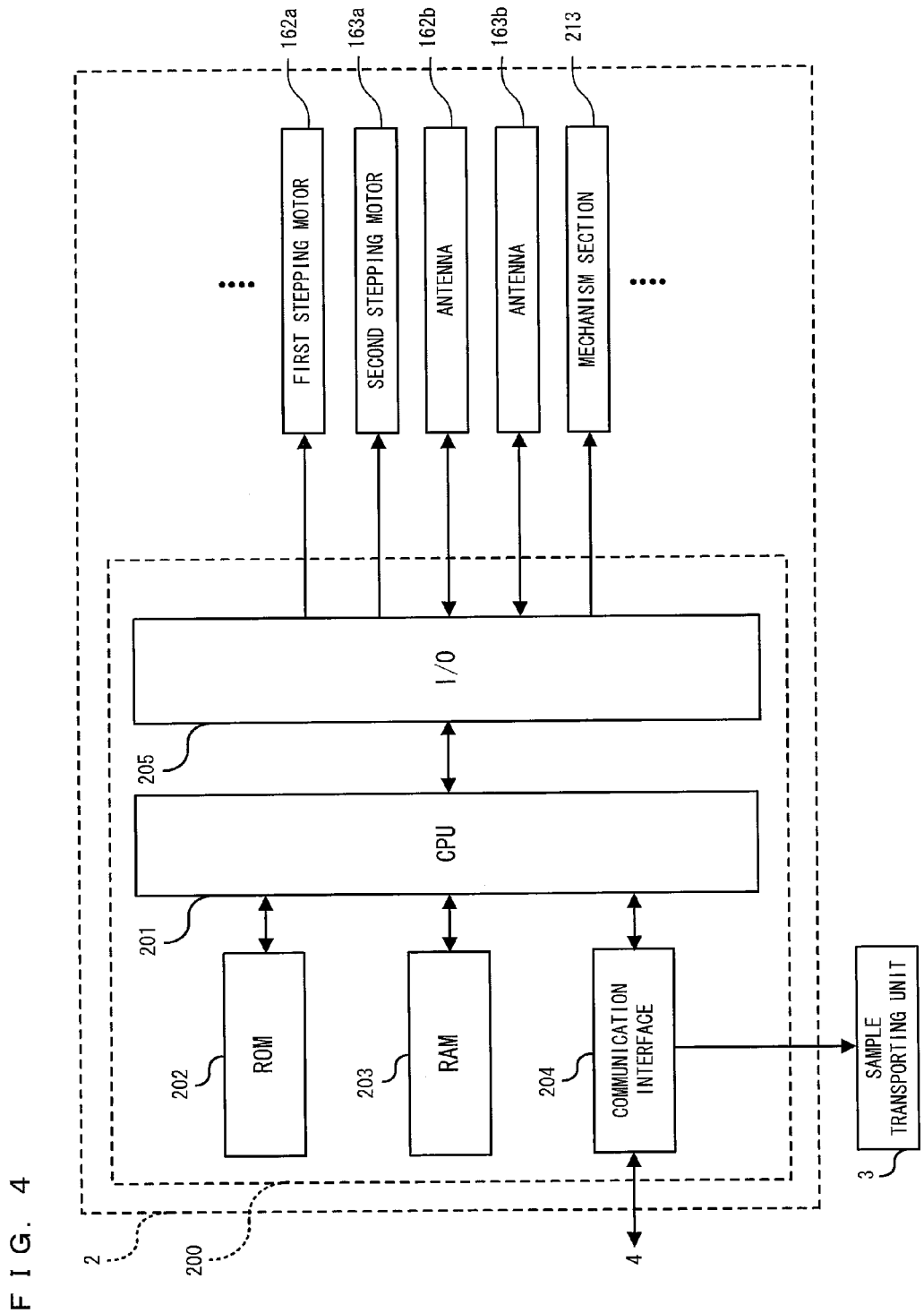
FIG. 4 is a block diagram showing a circuit configuration of a measurement apparatus included in a sample analyzer according to an embodiment.

FIG. 4 is a schematic diagram showing a circuit configuration of the measurement mechanism unit 2.

The measurement mechanism unit 2 includes a controller 200, the first stepping motor 162a, the second stepping motor 163a, the antennas 162b and 163b, and a mechanism section 213. The controller 200 includes a CPU 201, a ROM 202, a RAM 203, a communication interface 204, and an I/O interface 205.

The CPU 201 executes a computer program stored in the ROM 202 and a computer program loaded in the RAM 203. The RAM 203 is used for reading a computer program stored in the ROM 202, and is also used as a work area for the CPU 201 when the CPU 201 executes these computer programs.

The communication interface 204 is connected to the sample transporting unit 3 and the information processing apparatus 4. Via the communication interface 204, the CPU 201 transmits optical information about a sample (i.e., data of the amount of light generated by the reaction between the labeled antibody and the luminescent substrate) to the information processing apparatus 4, and receives signals from the information processing apparatus 4. The CPU 201 transmits an instruction signal to the sample transporting unit 3 via the communication interface 204 to drive the sample transporting unit 3.

The CPU 201 is connected to the first stepping motor 162a, the second stepping motor 163a, the antennas 162b and 163b, and the mechanism section 213, via the I/O interface 205.

The first stepping motor 162a and the second stepping motor 163a are independently driven under control of the CPU 201. The antennas 162b and 163b each read reagent management information of an RFID tag, under control of the CPU 201. The reagent management information read by the antennas 162b and 163b is outputted to the CPU 201 via the I/O interface 205 to be stored in the RAM 203. The mechanism section 213 includes other mechanisms in the measurement mechanism unit 2, and is driven under control of the CPU 201.

Figure 5:
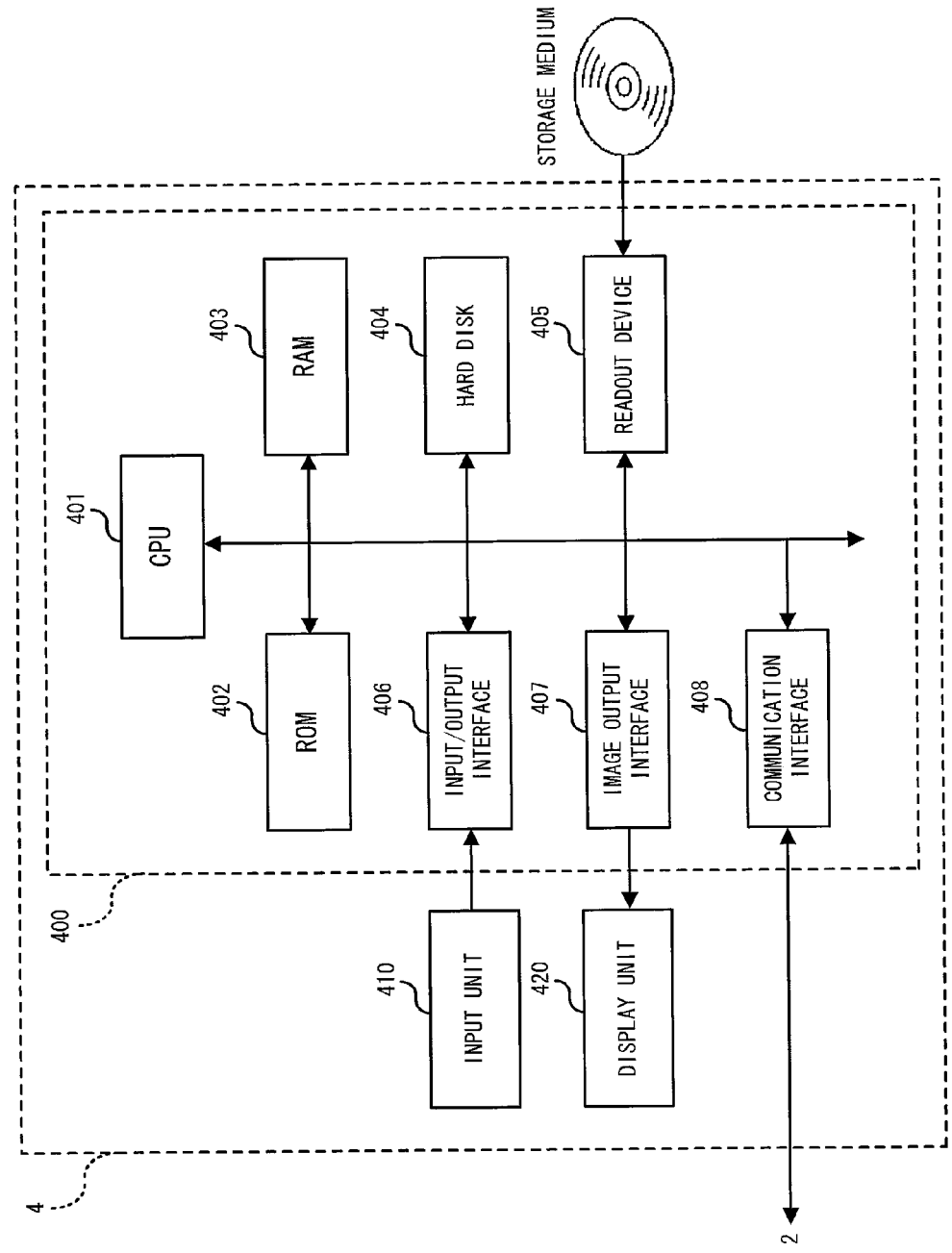
FIG. 5 is a block diagram showing a configuration of an information processing apparatus included in a sample analyzer according to an embodiment.

FIG. 5 is a schematic diagram showing a circuit configuration of the information processing apparatus 4.

The information processing apparatus 4 is structured as a personal computer, and includes the body 400, the input unit 410, and the display unit 420. The body 400 includes a CPU 401, a ROM 402, a RAM 403, a hard disk 404, a readout device 405, an input/output interface 406, an image output interface 407, and a communication interface 408.

The CPU 401 executes a computer program stored in the ROM 402 and a computer program loaded in the RAM 403. The RAM 403 is used for reading a computer program stored in the ROM 402 and the hard disk 404. The RAM 403 is also used as a work area for the CPU 401 when the CPU 401 executes these computer programs.

Various computer programs to be executed by the CPU 401, such as an operating system and application programs, and data used for executing these computer programs are installed in the hard disk 404. Specifically, there installed are: a program for performing, for example, display on the display unit 420 based on a reagent DB transmitted from the measurement mechanism unit 2; a program for transmitting an instruction to the measurement mechanism unit 2 based on an instruction received from the user via the input unit 410; and the like.

The hard disk 404 is provided with a reagent usage history database DB200. A usage history of a reagent used for each measurement item is recorded in the reagent usage history database DB200. FIG. 10 is a schematic diagram showing a structure of the reagent usage history database DB200. The reagent usage history database DB200 is structured, divided into seven days of the week, that is, from Monday to Sunday. Each cell of the reagent usage history database DB200 corresponds to one day, and the amount of a reagent used on the day is stored in the cell. As the "amount of a reagent", the number of tests (the number of times of measurements) performed by using the reagent is stored. In FIG. 10, a cell at a lower position corresponds to a newer date, and a cell at an upper position corresponds to an older date. A usage history of a reagent as described above is provided for each measurement item.

An operation day table is stored in the hard disk 404. FIG. 13 is a schematic diagram showing a structure of an operation day table. The operation day table OPT includes cells each corresponding to a date. Data "0" or "1" is stored in each cell. Here, "0" represents an "operation day", and thus, a day corresponding to a cell containing "0" is an "operation day". On the other hand, "1" represents a "non-business day" which is not an operation day, and thus, a day corresponding to a cell containing "1" is a "non-business day." Here, "non-business days" includes "regular holidays" which are established on a weekly basis at the facility where the sample analyzer 1 is installed, and "irregular holidays" which are not established on a weekly basis, such as public holidays. "Irregular holidays" includes holidays for the facility, such as a holiday provided once a year (such as foundation anniversary), in addition to public holidays. Since Saturdays and Sundays are "regular holidays", "1" is stored in all the cells corresponding to Saturdays and Sundays, as shown in FIG. 13. Calendar information containing holiday information such as public holidays and the foundation anniversary are stored in advance in the hard disk 404. Based on this calendar information, data "0" or "1" is stored in each cell in the operation day table OPT.

It should be noted that the user can freely set data "0" or "1" in a cell in the operation day table OPT via the input unit 410. Thus, it is possible to easily cope with a temporal holiday that has not been scheduled.

It should be noted that setting information that Saturdays and Sundays are "regular holidays" is stored in the hard disk 404.

Moreover, a database (hereinafter referred to as "reagent DB") of unique information of each reagent container and its corresponding reagent management information is created in the hard disk 404, in association with the holder on the inner table 162 or the outer table 163 where the reagent container is held.

Moreover, the hard disk 404 is provided with a user database in which information of each user who uses the sample analyzer 1 is stored. A user name, a password, a user group (a group category that defines the user's authority, such as "administrator" and "general user"), setting values for the user, and the like are stored in the user database, associated with each other. The setting values include a setting value for an initial screen (a menu screen or a maintenance status confirmation screen) that is displayed immediately after the user has logged on and displayed as a screen operable by the user.

Moreover, the hard disk 404 is provided with a database (hereinafter referred to as "maintenance information DB") for storing a maintenance operation schedule and a performance record on a daily basis. The maintenance information DB stores, in a calendar style, a maintenance operation to be performed and a record of the maintenance operation each day.

Moreover, the hard disk 404 is provided with a database regarding a bulletin board (hereinafter referred to as "bulletin board DB") used for information exchange among users. The bulletin board DB stores the user name of a user (hereinafter referred to as "contributor") who contributed a message to the bulletin board, and the content of the message, associated with each other.

The readout device 405 is implemented by a CD drive, a DVD drive, or the like, and can read a computer program and data stored in the storage medium. The input unit 410 implemented by a mouse and a keyboard is connected to the input/output interface 406, and data is inputted to the information processing apparatus 4 by an operator using the input unit 410.

The image output interface 407 is connected to the display unit 420 implemented by a display or the like, and outputs image signals that correspond to image data to the display unit 420. The display unit 420 displays an image based on the inputted image signals. The communication interface 408 enables data transmission to, and data reception from, the measurement mechanism unit 2.

[Operation of Sample Analyzer]

Figure 6:
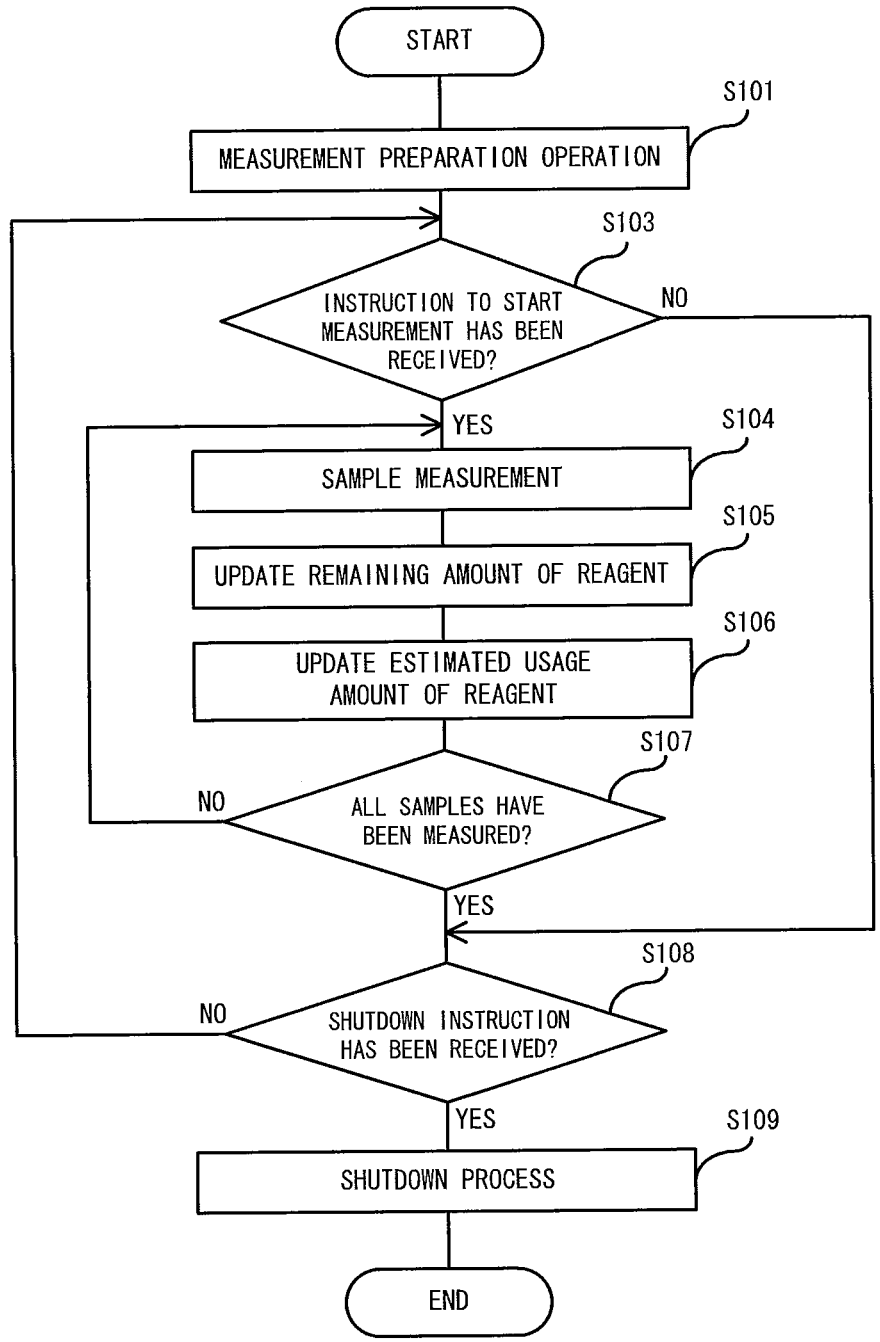
FIG. 6 is a flow chart showing operations performed by a sample analyzer according to an embodiment.

FIG. 6 is a flow chart showing operations performed by the sample analyzer 1. When the sample analyzer 1 is powered on by a user, the sample analyzer 1 performs a measurement preparation operation (step S101). Specifically, the CPU 401 obtains pieces of reagent management information read from an RFID tag of an R1/R3 reagent container and an RFID tag of an R2 reagent container 110 by the antennas 162*b* and 163*b*, respectively, and stores the pieces of reagent management information in the reagent DB provided in the hard disk 404. The measurement preparation operation will be described in detail below.

Figure 7A:
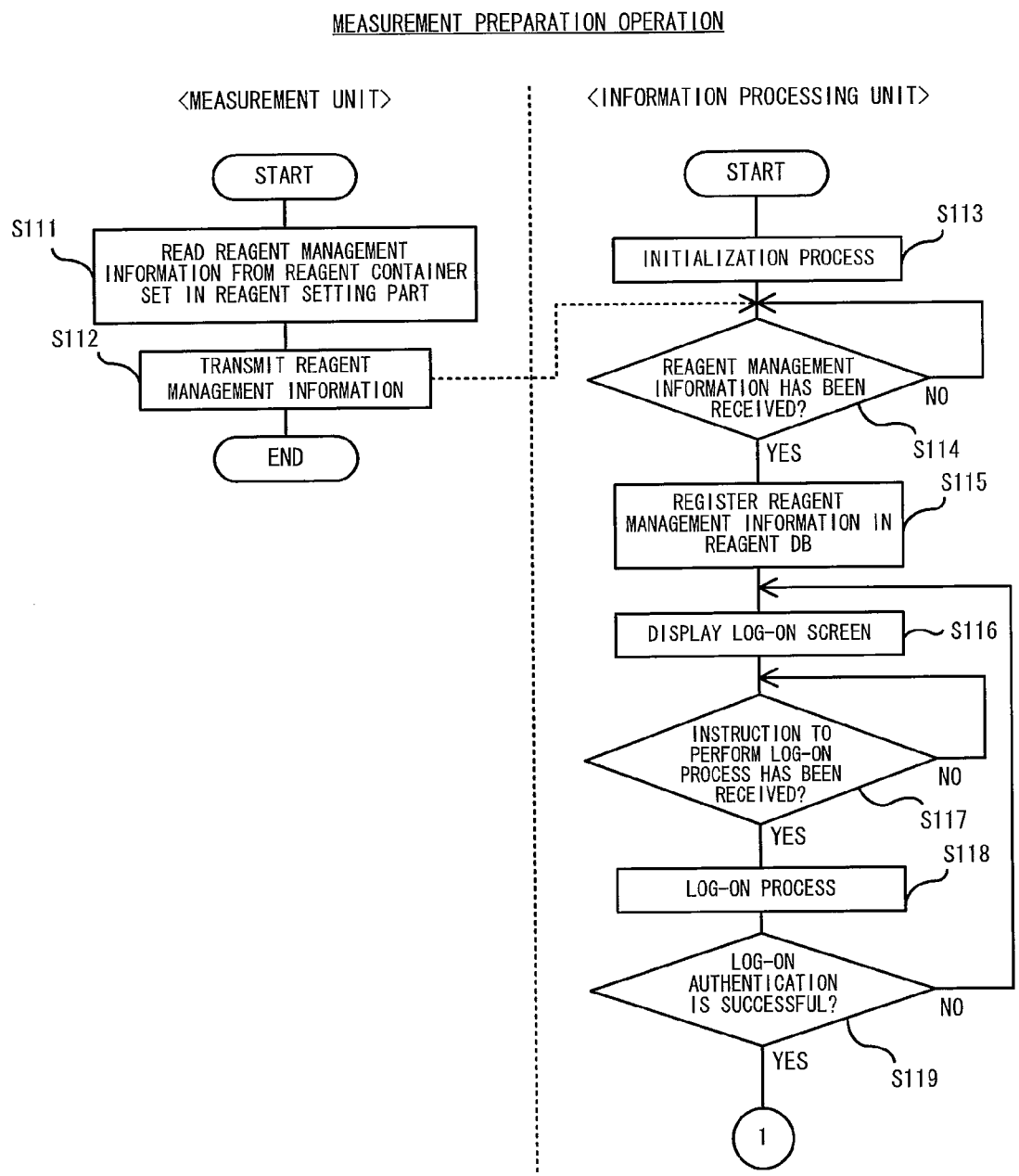
FIG. 7A is a flow chart (first half) showing the steps of a measurement preparation operation performed by a sample analyzer according to an embodiment.
Figure 7B:
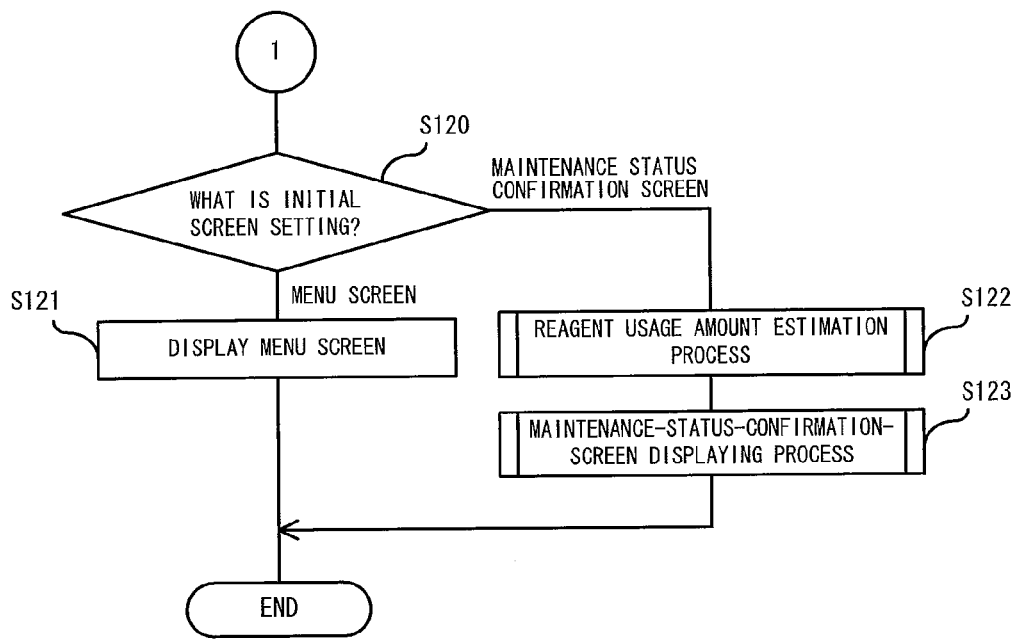
FIG. 7B is a flow chart (second half) showing the steps of the measurement preparation operation performed by a sample analyzer according to an embodiment.

FIG. 7A and FIG. 7B are a flow chart showing the steps of the measurement preparation operation performed by the sample analyzer 1. The measurement preparation operation is performed by the sample analyzer 1 immediately after the sample analyzer 1 is activated, and is a process for causing the sample analyzer 1 that is in a stationary state to enter a state which allows the sample analyzer 1 to perform sample analyses (measurement standby state). When the sample analyzer 1 is activated, the measurement unit 2 and the information processing unit 4 are powered on. First, operations performed by the measurement unit 2 will be described. When the sample analyzer 1 is activated, the R1/R3 reagent and the R2 reagent to be used on the day are set in the reagent setting part 16 of the measurement unit 2. When the sample analyzer 1 is powered on by the user, the CPU 201 of the measurement unit 2 causes the antennas 162*a* and 163*b* to read reagent management information from the RFID tag of an R1/R3 reagent container and reagent management information from the RFID tag of an R2 reagent container 110 set in the reagent setting part 16, respectively (step S111). The CPU 201 transmits the obtained reagent management information to the information processing unit 4 (step S112) and ends the process.

Next, operations performed by the information processing unit will be described. The CPU 401 of the information processing unit 4 initializes the hardware and the software (step S113) and determines whether the reagent management information transmitted from the measurement unit 2 has been received (step S114). When the reagent management information has not been received (NO in step S114), the CPU 401 repeats the process of step S114 and waits until receiving the reagent management information. Upon the information processing unit 4 receiving the reagent management information (YES in step S114), the CPU 401 registers the reagent management information in the reagent DB (step S115).

It should be noted that, in the reagent DB, the remaining amount (the remaining number of tests) of the R1 reagent container 100 and the remaining amount (the remaining number of tests) of the R3 reagent container 120 are stored separately. That is, with respect to the remaining amount in the reagent management information of the R1/R3 reagent container read in step S115, the remaining amount of the R1 reagent container 100 and the remaining amount of the R3 reagent container 120 are stored separately in the reagent DB.

Further, the CPU 401 causes the display unit 420 to display a log-on screen (step S116). The log-on screen is provided with input boxes for inputting a user name (user ID) and a password, respectively. The user inputs his or her user name and password in these input boxes, and issues an instruction to perform a log-on process. The CPU 401 determines whether an instruction to perform the log-on process (step S117) has been received. When the instruction to perform the log-on process has not been received (NO in step S117), the CPU 401 repeats the process of step S117 and waits until receiving the instruction to perform the log-on process. Upon receiving the instruction to perform the log-on process (YES in step S117), the CPU 401 performs the log-on process (step S118). In the log-on process, a log-on authentication is performed in which the user name and the password inputted on the log-on screen are verified against the user name and the password registered in the user database provided in the hard disk 404. When the log-on authentication has failed (NO in step S119), the CPU 401 causes the display unit 420 to display a log-on screen including a message for notifying the user of the failure of the log-on authentication (step S116).

When the log-on authentication has been successful (YES in step S119), the CPU 401 obtains a setting value of the user who has logged on, from the user database DB600, and determines whether a menu screen or a maintenance status confirmation screen is set as the initial screen that is to be displayed immediately after the log-on (step S120). The maintenance status confirmation screen is set as the default for the initial screen.

When the menu screen is set as the initial screen ("menu screen" in step S120), the CPU 401 causes the display unit 420 to display the menu screen (step S121), and ends the measurement preparation operation. Here, the menu screen is a screen from which various functions of the sample analyzer 1 can be called, and is provided with icons that correspond to various functions (such as a setting icon for calling a setting screen used for setting operations of the sample analyzer 1, a stored sample icon for displaying past results of measurements performed by the sample analyzer 1, and an order registration icon for calling an order registration screen used for registering a measurement order in the sample analyzer 1). The "icon" here is an image with which a specific function is associated and which is designed so as to symbolically represent the function. The "icon" includes images displayed in a window.

When the maintenance status confirmation screen is set as the initial screen ("maintenance status confirmation screen" in step S120), the CPU 401 performs a reagent usage amount estimation process (step S122). In the reagent usage amount estimation process of step S122, a usage amount of a reagent for the current day is estimated. As the "usage amount of a reagent" of the day, the number of tests (the number of times of measurements) that will be performed by using the reagent on the day is estimated. The reagent usage amount estimation process will be described later.

Next, the CPU 401 performs a maintenance-status-confirmation-screen displaying process (step S123), and causes the display unit 420 to display the maintenance status confirmation screen. The maintenance-status-confirmation-screen displaying process will be described in detail later. Then, the measurement preparation operation ends, whereby the sample analyzer 1 is set in the measurement standby state which allows the sample analyzer 1 to perform sample measurements.

After performing the above-described measurement preparation operation, the CPU 401 determines whether an instruction to start a measurement has been received from the user (step S103). When an instruction to start a measurement has not been received (NO in step S103), the CPU 401 advances the process to step S108. On the other hand, when an instruction to perform a sample measurement has been issued by the user, the CPU 401 receives this instruction (YES in step S103), and causes the measurement mechanism unit 2 to perform a sample measurement operation (step S104). In this measurement operation, a normal sample contained in a test tube located at the sample aspirating position 1a is aspirated, and this sample and the R1 to R3 reagents are mixed together, and then the mixture is subjected to measurement performed by the detector 14. Further, with respect to each reagent container from which respective reagents have been aspirated for the sample measurement, the CPU 401 updates (reduces) the remaining amounts of the R1 to R3 reagents in the reagent DB, in accordance with the aspirated amounts (step S105). In this case, the remaining amounts in the reagent DB are updated every time reagent aspiration is performed.

Further, based on the updated remaining amount of each reagent, the CPU 401 updates an estimated usage amount of the reagent (step S106). That is, when a reagent is consumed by one measurement, the estimated usage amount is reduced by the consumed amount. For example, in a case where an estimated usage amount of a reagent (the estimated number of tests) for a measurement item is 200, when one sample measurement is performed for the measurement item, the estimated usage amount of the reagent for the measurement item is reduced by 1. Therefore, in this case, the estimated usage amount of the reagent (the estimated number of tests) is updated to 199.

The CPU 401 determines whether there is a sample to be measured (step S107), and when there is a sample to be measured (NO in step S107), the CPU 401 returns the process to step S104 and continues the sample measurement (step S104). On the other hand, when the measurement has ended for all the samples (NO in step S107), the user issues a shutdown instruction to the sample analyzer 1. Upon receiving the shutdown instruction (YES in step S108), the CPU 401 performs a shutdown process (step S109) and ends the operations of the sample analyzer 1. On the other hand, when not having received the shutdown instruction (NO in step S108), the CPU 401 returns the process to step S103.

Figure 8:
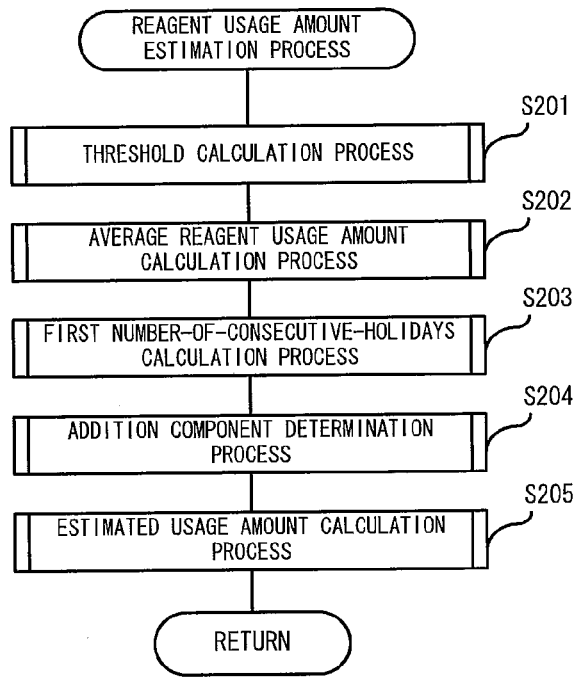
FIG. 8 is a flow chart showing the flow of a reagent usage amount estimation process.

Next, the reagent usage amount estimation process of step S122 will be described. FIG. 8 is a flow chart showing the flow of the reagent usage amount estimation process. Here, a case will be described where the current day is set as a target estimation day, for which a usage amount of the reagent is to be estimated.

With reference to FIG. 8, an outline of the reagent usage amount estimation process will be described. In the reagent usage amount estimation process, first, in a threshold calculation process of step S201, a threshold for determining data to be used in estimating a usage amount of the reagent is calculated. In this threshold calculation process, in a case where the target estimation day is, for example, Monday, there calculated is a threshold for extracting, from data of Mondays stored in the reagent usage history database DB200, only usage amounts of the reagent of operation days. This process prevents data of Mondays that were holidays from being reflected in an estimated usage amount. Therefore, it is possible to accurately estimate a usage amount of the reagent of the target estimation day that is an operation day.

Next, in an average reagent usage amount calculation process of step S202, there calculated is an average usage amount of the reagent per day that falls on the same day of the week as the target estimation day, by using the data extracted based on the threshold calculated in the threshold calculation process of step S201. For example, when the target estimation day is Monday, an average usage amount of the reagent per past Monday is calculated, based on only usage amounts of the reagent of operation days among data of Mondays stored in the reagent usage history database DB200.

Next, in a first number-of-consecutive-holidays calculation process of step S203, the number of "irregular holidays" that are before and consecutive to the target estimation day is determined. Then, in an addition component determination process of step S204, an addition component is determined in accordance with the number of days determined in the first number-of-consecutive-holidays calculation process of step S203. This addition component means a usage amount of the reagent to be added to the average usage amount of the reagent calculated in the average reagent usage amount calculation process of step S202. Then, in an estimated usage amount calculation process of step S205, a usage amount of the reagent for the target estimation day is calculated, by adding the usage amount determined in the addition component determination process of step S204 to the average usage amount of the reagent calculated in step S203.

Through the above processes, the usage amount of the reagent for the target estimation day is estimated. Next, each process will be described in detail.

In the threshold calculation process of step S201, there calculated are a first threshold and a second threshold, by using data recorded in the reagent usage history database DB200 excluding data of Saturdays and Sundays which are "regular holidays". These thresholds are used for determining data that is to be used in estimation of a usage amount of the reagent.

Figure 9:
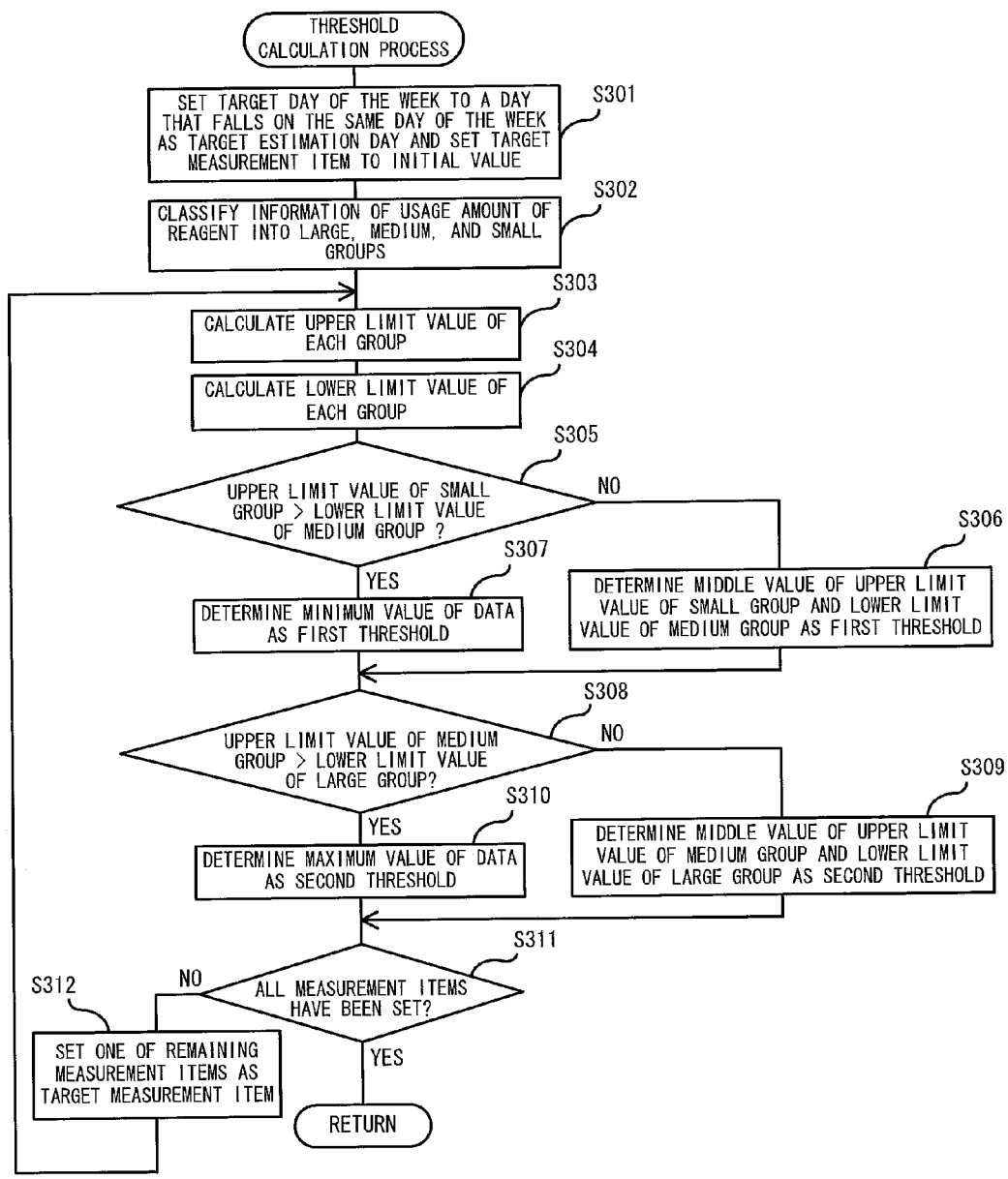
FIG. 9 is a flow chart showing the flow of a threshold calculation process.

FIG. 9 is a flow chart showing the flow of the threshold calculation process. First, the CPU 401 sets a target day of the week for which the thresholds are to be calculated, to the same day of the week as the target estimation day, and sets a target measurement item for which the thresholds are to be calculated, to an initial value (step S301). This initial value is determined in advance in the sample analyzer 1 (for example, "HBsAg" is an initial value for the target measurement item).

The CPU 401 reads, from the reagent usage history database DB200, pieces of usage amount information regarding the target measurement item that correspond to the target day of the week in the calendar, and classifies the read pieces of usage amount information into large, medium, and small groups (step S302).

Now, the process of step S302 will be described. When pieces of usage amount information are classified in terms of measurement items and days of the week, they are roughly classified into three groups. When the facility is off, sample tests are basically not performed except for samples that need test results immediately. Therefore, usage amount information on the day when the facility is off belongs to a group that corresponds to the least usage amount (hereinafter referred to as a "small group"). On the other hand, when the facility is not off, since a lot of sample tests are performed, the usage amount of the reagent is increased. Especially, in a case where the preceding day is an irregular holiday (or a case where two days before is an irregular holiday when the preceding day is a regular holiday,) the number of sample tests is greatly increased. This is because, since sample tests cannot be performed on an irregular holiday, many samples are tested on a next operation day. Therefore, usage amount information for an operation day whose preceding day is an irregular holiday belongs to a group that corresponds to a largest usage amount (hereinafter referred to as a "large group"). On an operation day whose preceding day is not an irregular holiday, a typical number of sample tests are performed. Therefore, usage amount information of an operation day whose preceding day is not an irregular holiday belongs to a group that corresponds to a moderate usage amount (hereinafter referred to as a "medium group"). For example, of the usage amount information of Tuesdays in FIG. 10, "160", "170", "181", "178", "175", "169", "170", "179", and "168" belong to the medium group, "5", "34", "4", and "6" belong to the small group, and "210" belongs to the large group. In the process of step S302, the read pieces of usage amount information are arranged in a descending order, and then a difference between respective adjacent pieces of usage amount information is calculated. Then, at two positions where the difference is especially large, the pieces of usage amount information are classified into the large group, the medium group, and the small group.

When the process of step S302 ends, the CPU 401 calculates the upper limit value of each group (step S303). In this process, the average value+3SD of the usage amount information in each group is set as the upper limit value for the group. That is, the upper limit value of the large group is the average value+3SD of the usage amount information belonging to the large group, the upper limit value of the medium group is the average value+3SD of the usage amount information belonging to the medium group, and the upper limit value of the small group is the average value+3SD of the usage amount information belonging to the small group.

Next, the CPU 401 calculates the lower limit value of each group (step S304). In this process, the average value−3SD of the usage amount information in each group is set as the lower limit value of the group.

Figure 11A:
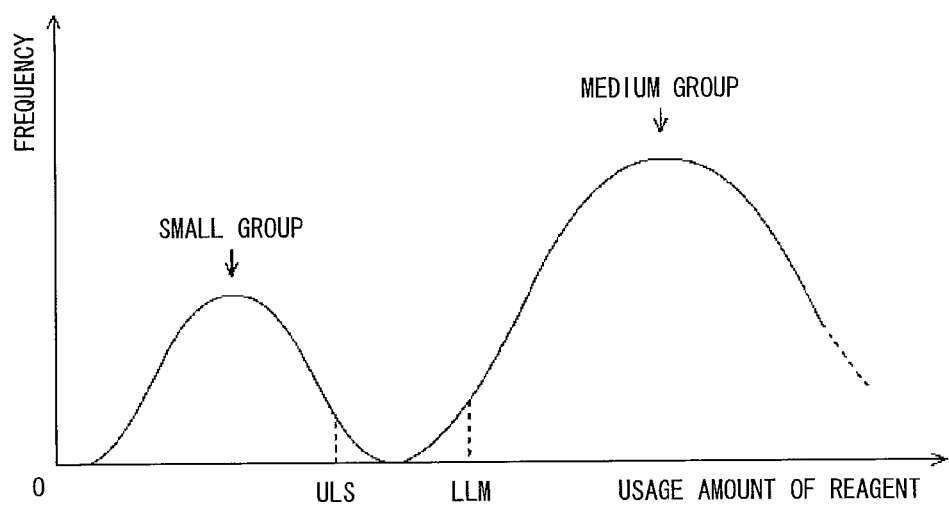
FIG. 11A is a schematic diagram showing an example of relationship between the lower limit value of a medium group and the upper limit value of a small group.

Next, the CPU 401 determines whether the calculated upper limit value of the small group is greater than the lower limit value of the medium group (step S305). This process will be described below. FIG. 11A is a schematic diagram showing an example of relationship between the lower limit value of the medium group and the upper limit value of the small group. In the example shown in FIG. 11A, the lower limit value LLM of the medium group is greater than the upper limit value ULS of the small group. In this case, the medium group and the small group are clearly separated from each other. When the upper limit value of the small group is lower than or equal to the lower limit value of the medium group as in this case (NO in step S305), the CPU 401 determines a middle value between the lower limit value of the medium group and the lower limit value of the small group as the first threshold for determining data to be used in estimation of a usage amount of the reagent (step S306). Then, the CPU 401 advances the process to step S308.

Figure 11B:
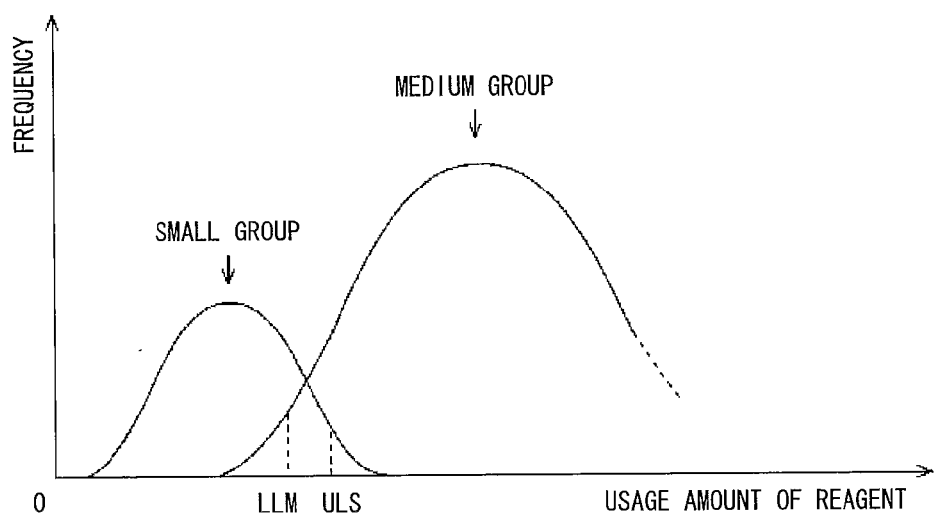
FIG. 11B is a schematic diagram showing another example of relationship between the lower limit value of a medium group and the upper limit value of a small group.

FIG. 11B is a schematic diagram showing another example of relationship between the lower limit value of the medium group and the upper limit value of the small group. In the example shown in FIG. 11B, the lower limit value LLM of the medium group is smaller than the upper limit value ULS of the small group. In this case, the medium group and the small group are not clearly separated from each other. When the upper limit value of the small group is greater than the lower limit value of the medium group as in this case (YES in step S305), the CPU 401 determines a minimum value for the target measurement item in the usage amount information of the target day of the week, as the first threshold for determining data to be used in estimation of a usage amount of the reagent (step S307). Then, the CPU 401 advances the process to step S308.

In step S308, the CPU 401 determines whether the calculated upper limit value of the medium group is greater than the lower limit value of the large group (step S308). When the lower limit value of the large group is greater than the upper limit value of the medium group, the large group and the medium group are clearly separated from each other. When the upper limit value of the medium group is smaller than or equal to the lower limit value of the large group as in this case (NO in step S308), the CPU 401 determines a middle value between the lower limit value of the large group and the lower limit value of the medium group, as the second threshold for determining data to be used in estimation of a usage amount of the reagent (step S309). Then, the CPU 401 advances the process to step S311.

When the lower limit value of the large group is smaller than the upper limit value of the medium group, the large group and the medium group are not clearly separated from each other. When the upper limit value of the medium group is greater than the lower limit value of the large group as in this case (YES in step S308), the CPU 401 determines a maximum value for the target measurement item in the usage amount information of the target day of the week, as the second threshold for determining data to be used in estimation of a usage amount of the reagent (step S310). Then, the CPU 401 advances the process to step S311.

In step S311, the CPU 401 determines whether all measurement items have already been set as target measurement items (step S311). When there are measurement items remaining that have not been set as target measurement items (NO in step S311), the CPU 401 sets one of the remaining measurement items as a target measurement item (step S312), and returns the process to step S302.

On the other hand, in step S311, when all measurement items have been set as target measurement items (YES in step S311), the CPU 401 returns the process to the address for calling the threshold calculation process in the reagent usage amount estimation process.

Figure 12:
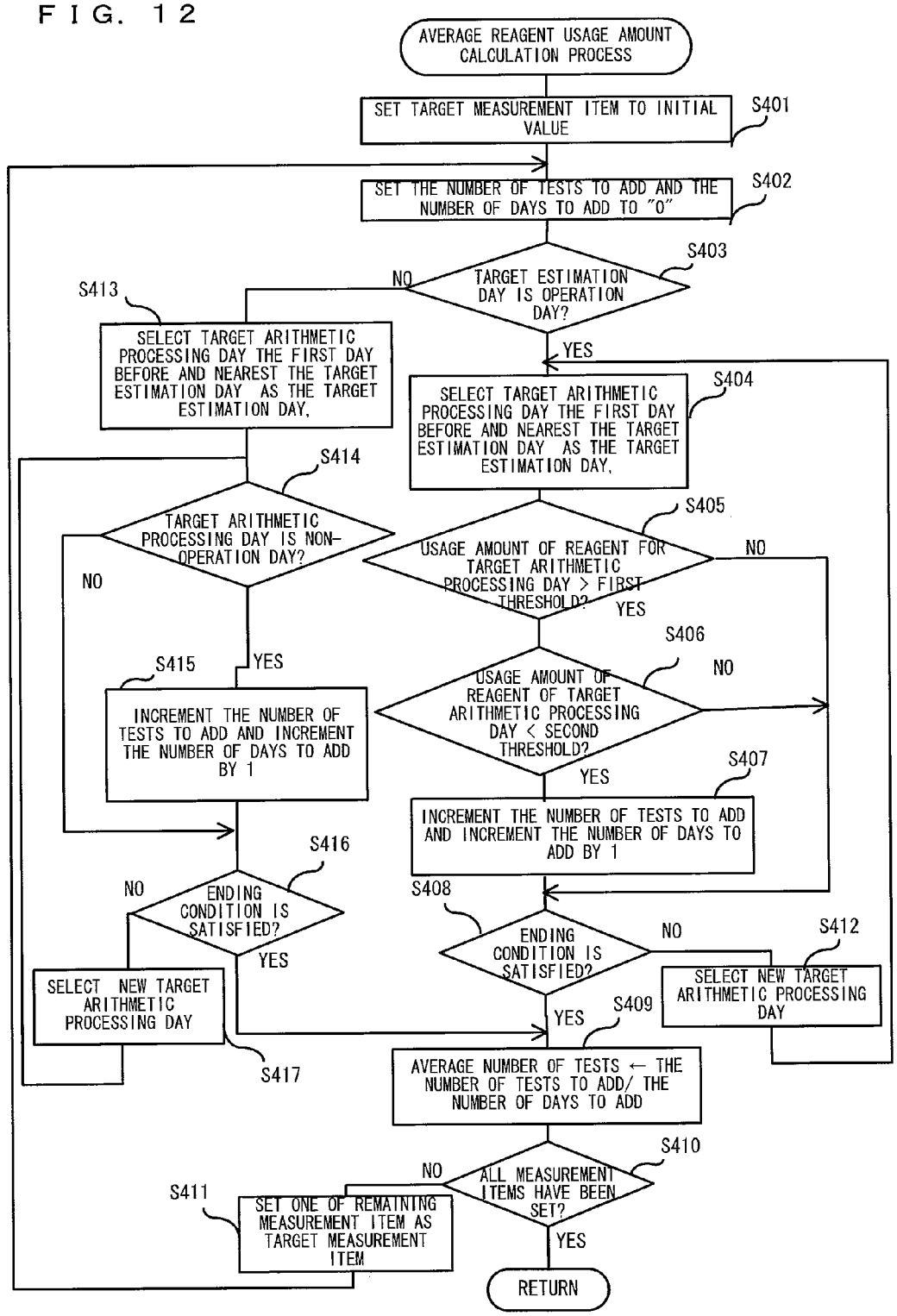
FIG. 12 is a flow chart showing the flow of an average reagent usage amount calculation process.

After ending the above-described threshold calculation process, the CPU 401 performs the average reagent usage amount calculation process (step S202). FIG. 12 is a flow chart showing the flow of the average reagent usage amount calculation process. First, the CPU 401 sets the target measurement item for which an average usage amount of the reagent is to be calculated, to an initial value (step S401). This initial value is the same as the initial value used for the measurement item in step S301.

Next, the CPU 401 sets the number of tests to add and the number of days to add, which are parameters used in calculation of an average usage amount of the reagent, to an initial value "0" (step S402).

Next, the CPU 401 determines whether the target estimation day is an operation day (step S403). This process will be described below.

In the process of step S403, whether the target estimation day is an operation day is determined by referring to the operation day table OPT described above. That is, the CPU 401 confirms the content of the cell that corresponds to the target estimation day in the operation day table OPT. If "0" is stored, the CPU 401 determines that the target estimation day is an "operation day" and if "1" is stored, the CPU 401 determines that the target estimation day is a "non-operation day" (a regular holiday or an irregular holiday).

When the target estimation day is an "operation day" in step S403 (YES in step S403), the CPU 401 selects, from among days that fall on the same day of the week as the target estimation day, the first day that is before and nearest the target estimation day, as a target arithmetic processing day (step S404). For example, when the target estimation day is Monday, last Monday is selected as the target arithmetic processing day.

Next, the CPU 401 determines whether the usage amount of the reagent of the target arithmetic processing day is greater than the first threshold (step S405). The first threshold is a lower limit value for selecting, from among past usage amounts of the reagent, a usage amount of the reagent to be used in calculation of an average usage amount of the reagent. Therefore, when the usage amount of the reagent of the target arithmetic processing day is less than or equal to the first threshold (NO in step S405), the CPU 401 advances the process to step S408, and this usage amount of the reagent is not used for calculation of an average usage amount of the reagent.

On the other hand, when the usage amount of the reagent of the target arithmetic processing day is greater than the first threshold in step S405 (YES in step S405), the CPU 401 determines whether the usage amount of the reagent of the target arithmetic processing day is smaller than the second threshold (step S406). The second threshold is an upper limit value for selecting, from among past usage amounts of the reagent, a usage amount of the reagent to be used in calculation of an average usage amount of the reagent. Therefore, when the usage amount of the reagent is greater than or equal to the second threshold (NO in step S406), the CPU 401 advances the process to step S408, and this usage amount of the reagent is not used in calculation of an average usage amount of the reagent.

When the usage amount of the reagent of the target arithmetic processing day is smaller than the second threshold in step S406 (YES in step S406), this usage amount of the reagent is to be used in calculation of an average usage amount of the reagent. In this case, the CPU 401 sets a result obtained by adding the usage amount of the reagent (the number of tests) of the target arithmetic processing day to the number of tests to add, as a new number of tests to add, and increments the number of days to add by 1 (step S407). Then, the CPU 401 advances the process to step S408.

In step S408, the CPU 401 determines whether an ending condition is satisfied (step S408). Here, the ending condition is that the number of days to add is greater than 10, or that no usage amount of the reagent before the target arithmetic processing day is registered in the reagent usage history database DB200. Here, when the number of days to add is greater than 10, or no usage amount of the reagent before the target arithmetic processing day is registered in the reagent usage history database DB200 (YES in step S408), the CPU 401 sets a result obtained by dividing the number of tests to add by the number of days to add, as an average usage amount of the reagent (an average number of tests) (step S409), and then determines whether all measurement items have been set as target measurement items (step S410). When there are measurement items remaining that have not been set as target measurement items (NO in step S410), the CPU 401 sets one of the remaining measurement items as a target measurement item (step S411), and returns the process to step S402.

On the other hand, when all measurement items have been set as target measurement items in step S411 (YES in step S410), the CPU 401 returns the process to the address for calling the average reagent usage amount calculation process in the reagent usage amount estimation process.

When the ending condition is not satisfied, that is, when the number of days to add is smaller than 10 and there is a usage amount of the reagent before the target arithmetic processing day registered in the reagent usage history database DB200 in step S408, (NO in step S408), the CPU 401 selects a day, in the preceding week of the target arithmetic processing day, that falls on the same day of the week as the target arithmetic processing day, as a new target arithmetic processing day (step S412), and then, returns the process to step S405.

Next, a case where the target estimation day is a "non-operation day" in step S403 will be described. When the target estimation day is a "non-operation day" in step S403 (NO in step S403), an average usage amount of the reagent that is a usage amount of the reagent in a non-operation day is calculated in the following manner. First, the CPU 401 selects, from among days that fall on the same day of the week as the target estimation day, the first day that is before and nearest the target estimation day, as a target arithmetic processing day (step S413).

Next, the CPU 401 determines whether the target arithmetic processing day is set as a non-operation day in the operation day table, and whether the usage amount of the reagent of the target arithmetic processing day is less than or equal to the first threshold (step S414). In this process, it is determined whether the target arithmetic processing day is a non-operation day. Specifically, when "1" is set for the target arithmetic processing day in the operation day table OPT, it is determined that the target arithmetic processing day is a non-operation day. However, there may be a case where information of non-operation days is not accurately set in the operation day table OPT. Therefore, in the present embodiment, when the usage amount of the reagent of the target arithmetic processing day in the reagent usage history database DB200 is less than or equal to the first threshold, which means the usage amount of the reagent of the target arithmetic processing day is very small, such a target arithmetic processing day is estimated to be a non-operation day.

When the target arithmetic processing day is set as a non-operation day in the operation day table or the usage amount of the reagent of the target arithmetic processing day is less than or equal to the first threshold in step S414 (YES in step S414), the target arithmetic processing day is determined to correspond to a non-operation day, and the CPU 401 sets a result obtained by adding the usage amount of the reagent of the target arithmetic processing day to the number of tests to add, as a new number of tests to add, and increments the number of days to add by 1 (step S415), and then advances the process to step S416.

On the other hand, in step S414, when the target arithmetic processing day is not set as a non-operation day in the operation day table (that is, "0" is set for the target arithmetic processing day) and the usage amount of the reagent of the target arithmetic processing day is greater than the first threshold (NO in step S414), the target arithmetic processing day is determined as not corresponding to a non-operation day. In this case, the CPU 401 advances the process to step S416.

In step S416, the CPU 401 determines whether an ending condition is satisfied (step S416). The ending condition is the same as the ending condition in step S408. Specifically, when the number of days to add is greater than 10 or no usage amount of the reagent before the target arithmetic processing day is registered in the reagent usage history database DB200 (YES in step S416), the CPU 401 sets a result obtained by dividing the number of tests to add by the number of days to add, as an average usage amount of the reagent (step S409), and then determines whether all measurement items have been set as target measurement items (step S410). When there are measurement items remaining that have not been set as target measurement items (NO in step S410), the CPU 401 sets one of the remaining measurement items as a target measurement item (step S411), and returns the process to step S402.

When all measurement items have been set as target measurement items in step S410, (YES in step S410), the CPU 401 returns the process to the address for calling the average reagent usage amount calculation process in the reagent usage amount estimation process.

When the ending condition is not satisfied in step S416, that is, when the number of days to add is smaller than 10 and there is a usage amount of the reagent before the target arithmetic processing day registered in the reagent usage history database DB200 (NO in step S416), the CPU 401 selects a day, in the preceding week of the target arithmetic processing day, that falls on the same day of the week as the target arithmetic processing day, as a new target arithmetic processing day (step S417), and then returns the process to step S414.

Figure 14:
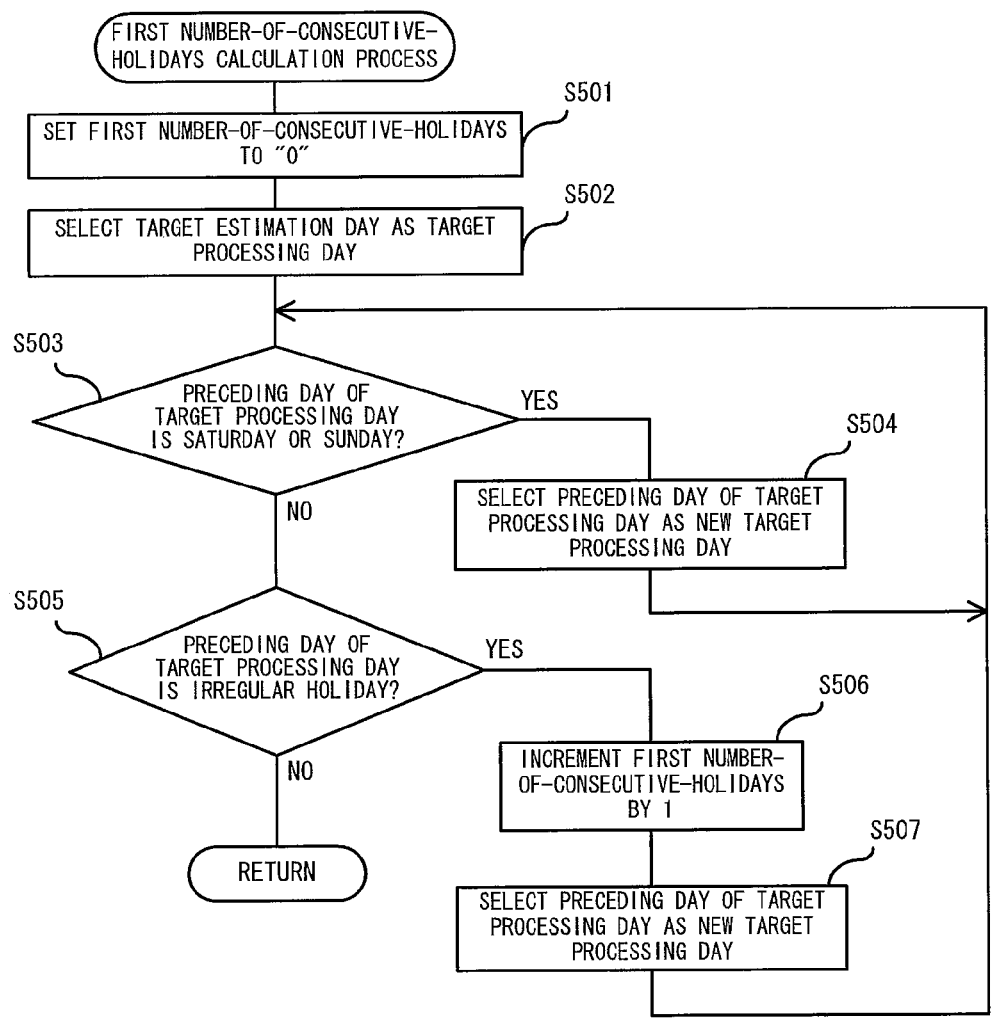
FIG. 14 is a flow chart showing the flow of a first number-of-consecutive-holidays calculation process.

After ending the average reagent usage amount calculation process described above, the CPU 401 performs the first number-of-consecutive-holidays calculation process (step S203). FIG. 14 is a flow chart showing the flow of the first number-of-consecutive-holidays calculation process. On an operation day whose preceding day (two days before when the preceding day is a regular holiday) is an irregular holiday, it is general that the number of sample tests is increased than that of an ordinary operation day (an operation day whose preceding day is not an irregular holiday) because sample tests were not performed on the irregular holiday. On an operation day after consecutive irregular holidays, since the number of days on which sample tests were not performed is further increased, the number of sample tests tends to increase in accordance with the number of the consecutive irregular holidays. Therefore, for an accurate estimation of a usage amount of the reagent, it is necessary to estimate the usage amount of the reagent in accordance with the number of consecutive irregular holidays immediately before the target estimation day. That is, by correcting the average usage amount of the reagent in accordance with the number of consecutive irregular holidays, it is possible to accurately estimate a usage amount of the reagent. In the first number-of-consecutive-holidays calculation process, the number of consecutive irregular holidays immediately before the target estimation day is determined.

First, the CPU 401 sets a parameter "first number-of-consecutive-holidays" to an initial value "0" (step S501), and selects the target estimation day as a target processing day (step S502).

Next, the CPU 401 determines whether the preceding day of the target processing day is Saturday or Sunday (step S503). The first number-of-consecutive-holidays calculation process is a process of calculating the number of consecutive irregular holidays, and regular holidays of the facility is not included in the consecutive number. In step S503, whether the preceding day of the target processing day is Saturday or Sunday is determined. The reason for providing this process is as follows. Since regular holidays of the facility are also non-operation days, it is general that the number of sample tests extremely decreases. However, a usage amount of the reagent is estimated based on the average usage amount of the reagent of days that fall on the same day of the week as the target estimation day. Therefore, when the target estimation day is Monday (which is immediately after a regular holiday), the average usage amount of the reagent of past Mondays is used. Here, since the preceding day of and the two days before every Monday are regular holidays, the fact that the preceding day and the two days before are regular holidays is already reflected on the average usage amount of the reagent. Therefore, when estimating a usage amount of the reagent for a target estimation day whose preceding day is a regular holiday, it is not necessary to correct the average usage amount of the reagent due to the fact that the preceding day is a regular holiday. However, when the preceding day of the target estimation day is a regular holiday and the day immediately before the regular holiday is an irregular holiday (for example, in the case of Monday when last Friday is a holiday), the number of sample tests increases compared with that of an ordinary operation day whose preceding day only is a regular holiday (for example, when the day immediately before a regular holiday is not a holiday, such as Monday when last Friday is not a holiday). Therefore, in this case, it is necessary to correct the average usage amount of the reagent by an amount that will reflect the fact that the preceding day of a regular holiday is a holiday.

When the preceding day of the target processing day is Saturday or Sunday in step S503 (YES in step S503), the CPU 401 selects the preceding day of the target processing day as a new target processing day (step S504), and then returns the process to step S503.

When the preceding day of the target processing day is neither Saturday nor Sunday in step S503 (NO in step S503), the CPU 401 determines whether the preceding day of the target processing day is an irregular holiday (step S505). When the preceding day of the target processing day is an irregular holiday (YES in step S505), the CPU 401 increments by 1 the parameter "first number-of-consecutive-holidays" (step S506), selects the preceding day of the target processing day as a new target processing day (step S507), and then returns the process to step S503.

On the other hand, when the preceding day of the target processing day is not an irregular holiday in step S505 (NO in step S505), the CPU 401 returns the process to the address for calling the first number-of-consecutive-holidays calculation process in the reagent usage amount estimation process.

Figure 15:
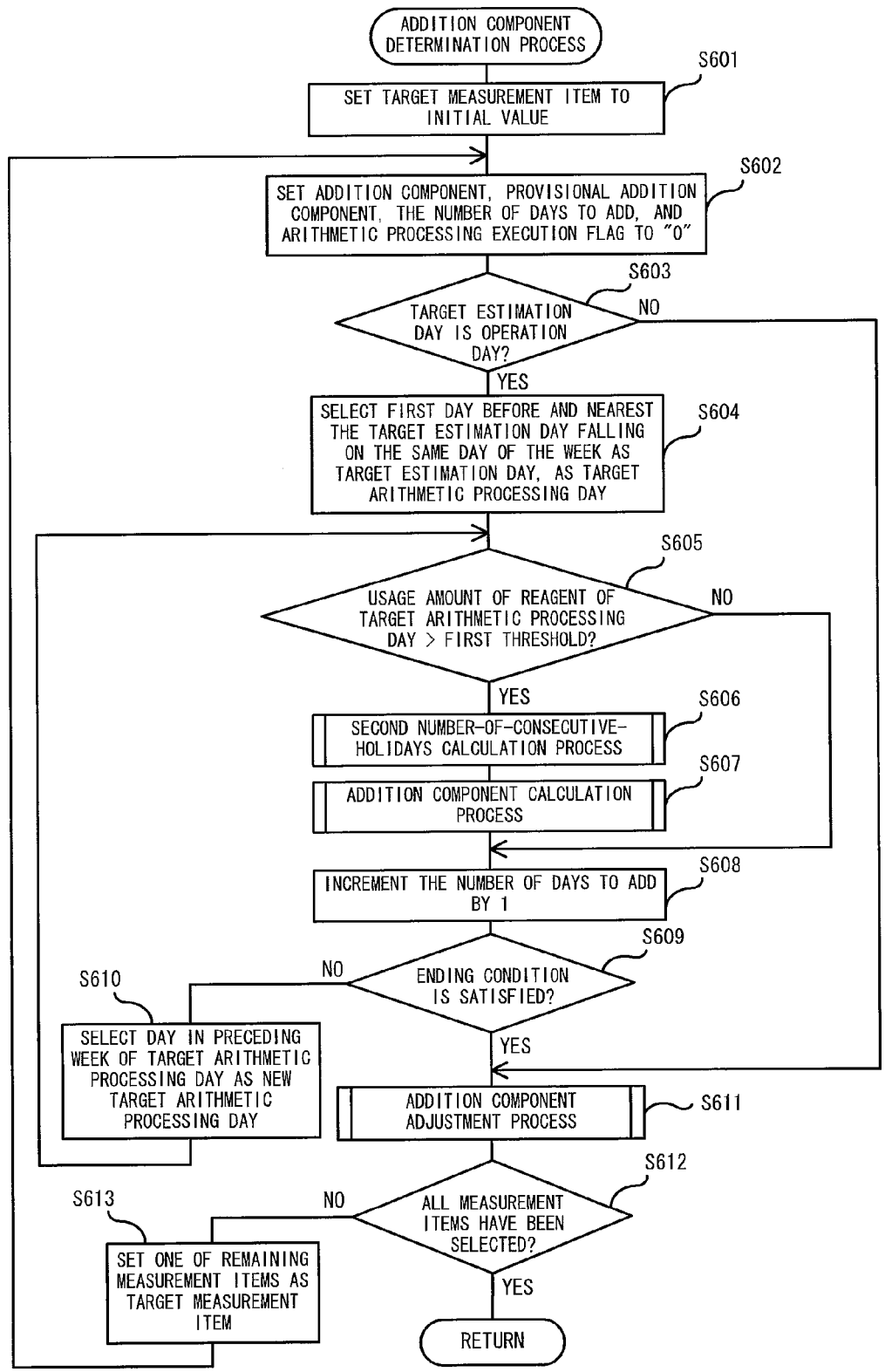
FIG. 15 is a flow chart showing the flow of an addition component determination process.

After ending the first number-of-consecutive-holidays calculation process described above, the CPU 401 performs the addition component determination process (step S204). FIG. 15 is a flow chart showing the flow of the addition component determination process. As described above, in the present embodiment, when there is an irregular holiday immediately before the target estimation day, an estimated usage amount of the reagent is determined by correcting the average usage amount of the reagent. In the addition component determination process, an addition component to be used in the correction of the average usage amount of the reagent is determined.

First, the CPU 401 sets the target measurement item for which an addition component is to be calculated, to an initial value (step S601). This initial value is the same as the initial value used for the measurement item in step S301 and step S401.

Next, the CPU 401 sets each of an addition component, a provisional addition component, the number of days to add, and an arithmetic processing execution flag, which are parameters used in the arithmetic processing for determining the addition component, to an initial value "0" (step S602).

Next, the CPU 401 determines whether the target estimation day is an operation day (step S603). This process is a process similar to that of step S403, and uses the operation day table OPT.

When the target estimation day is an operation day (YES in step S603), the CPU 401 selects, from among days that fall on the same day of the week as the target estimation day, the first day that is before and nearest the target estimation day, as a target arithmetic processing day (step S604). For example, when today (Monday) is a target estimation day, last Monday is selected as the target arithmetic processing day.

Next, the CPU 401 determines whether the usage amount of the reagent of the target arithmetic processing day is greater than the first threshold (step S605). In this process, the first threshold is used in order to determine whether the target arithmetic processing day that falls on the same day of the week as the target estimation day is an operation day or a non-operation day. That is, if the usage amount of the reagent is greater than the first threshold, the target arithmetic processing day is determined to be an operation day, and if the usage amount of the reagent is less than or equal to the first threshold, the target arithmetic processing day is determined to be a non-operation day.

When the usage amount of the reagent of the target arithmetic processing day is greater than the first threshold in step S605 (YES in step S605), a relatively large usage amount of the reagent is expected because the target arithmetic processing day is an operation day. In such a case, a second number-of-consecutive-holidays calculation process and an addition component calculation process which are described below are performed, whereby data to be used in determination of the addition component is determined.

Figure 16:
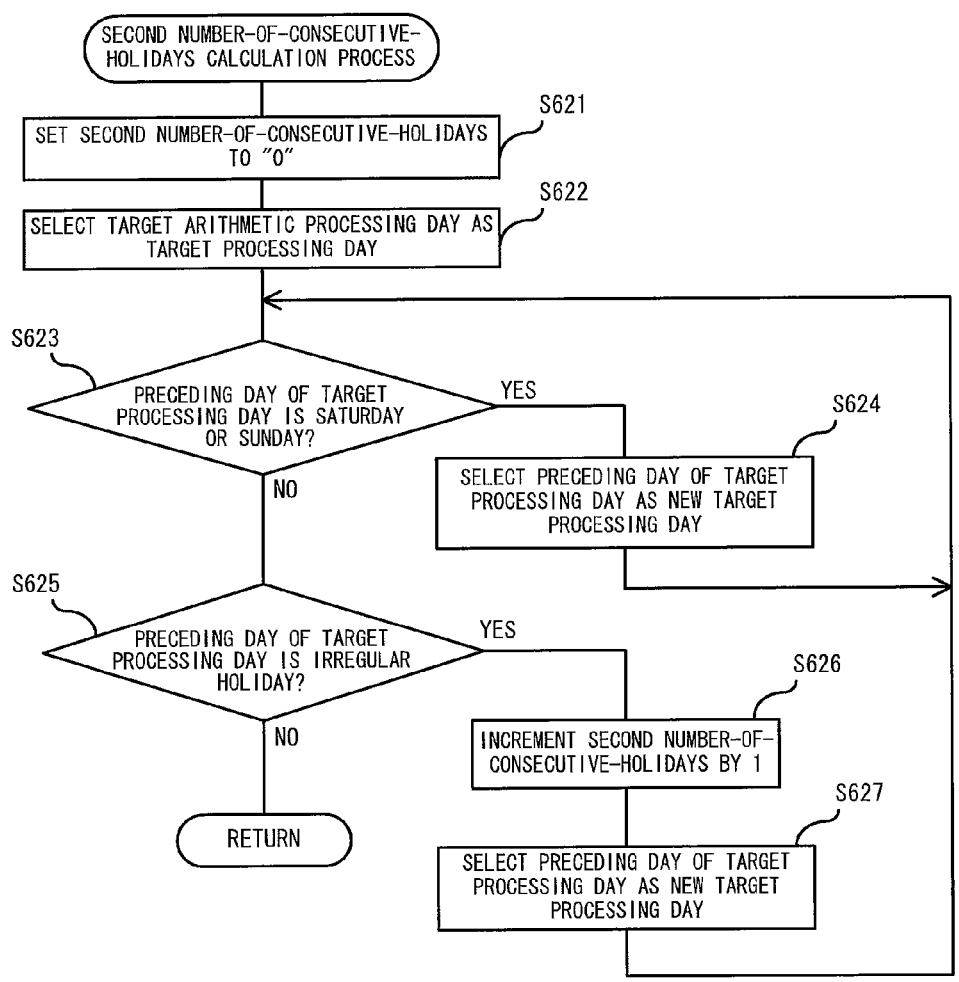
FIG. 16 is a flow chart showing the flow of a second number-of-consecutive-holidays calculation process.

When the usage amount of the reagent of the target arithmetic processing day is greater than the first threshold in step S605 (YES in step S605), the CPU 401 performs the second number-of-consecutive-holidays calculation process (step S606), first. FIG. 16 is a flow chart showing the flow of the second number-of-consecutive-holidays calculation process. In this process, the value of a "second number-of-consecutive-holidays" is calculated, which shows the number of consecutive irregular holidays immediately before the target arithmetic processing day.

First, the CPU 401 sets a parameter "second number-of-consecutive-holidays" to an initial value "0" (step S621), and selects the target arithmetic processing day as the target processing day (step S622).

Next, the CPU 401 determines whether the preceding day of the target processing day is Saturday or Sunday (step S623). When the preceding day of the target processing day is Saturday or Sunday in step S623 (YES in step S623), the CPU 401 selects the preceding day of the target processing day as a new target processing day (step S624), and returns the process to step S623.

When the preceding day of the target processing day is neither Saturday nor Sunday in step S623 (NO in step S623), the CPU 401 determines whether the preceding day of the target processing day is an irregular holiday (step S625). When the preceding day of the target processing day is an irregular holiday (YES in step S625), the CPU 401 increments by 1 the parameter "second number-of-consecutive-holidays" (step S626), selects the preceding day of the target processing day as a new target processing day (step S627), and returns the process to step S623.

On the other hand, when the preceding day of the target processing day is not an irregular holiday in step S625 (NO in step S625), the CPU 401 returns the process to the address for calling the second number-of-consecutive-holidays calculation process in the addition component determination process.

Figure 17:
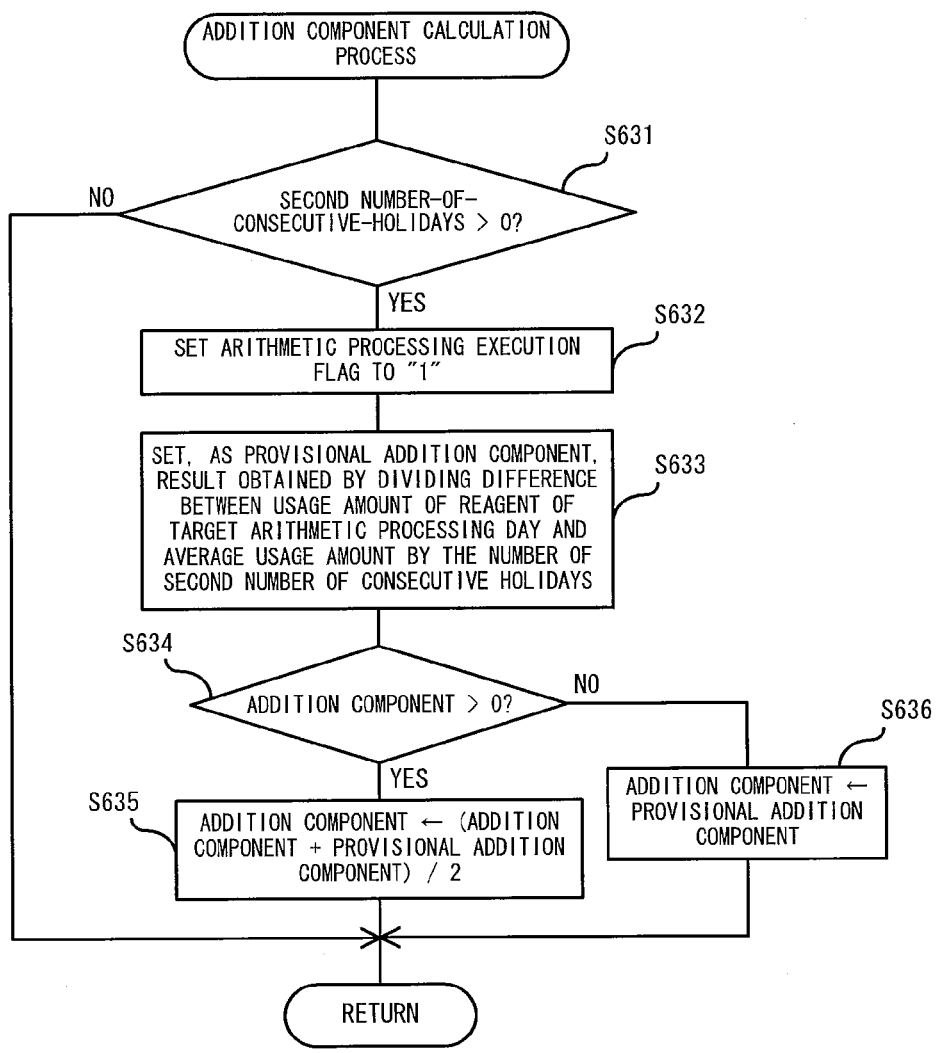
FIG. 17 is a flow chart showing the flow of an addition component calculation process.

When the second number-of-consecutive-holidays calculation process as described above ends, the CPU 401 performs the addition component calculation process (step S607). FIG. 17 is a flow chart showing the flow of the addition component calculation process. In this process, arithmetic processing for determining an addition component is performed.

First, the CPU 401 determines whether the second number-of-consecutive-holidays is greater than "0", that is, whether there is an irregular holiday immediately before the target arithmetic processing day (step S631). When the second number-of-consecutive-holidays is greater than "0", that is, when there is an irregular holiday immediately before the target arithmetic processing day (YES in step S631), the CPU 401 sets the arithmetic processing execution flag to "1" (step S632). This arithmetic processing execution flag is information that indicates whether arithmetic processing regarding the addition component has been performed at least once. When "0" is set, it means that no arithmetic processing regarding the addition component has been performed, and when "1" is set, it means that arithmetic processing regarding the addition component has been performed at least once. That is, when the second number-of-consecutive-holidays is greater than "0", since arithmetic processing regarding the addition component is to be performed, the arithmetic processing execution flag is set to "1".

Next, the CPU 401 determines a difference between the usage amount of the reagent of the target arithmetic processing day and the average usage amount of the reagent, and sets the result obtained by dividing the difference by the second number-of-consecutive-holidays, as a provisional addition component (step S633). For example, when the preceding day of the target arithmetic processing day is an irregular holiday and thus the usage amount of the reagent of the target arithmetic processing day is greater than that of an ordinary operation day that falls on the same day of the week as the target arithmetic processing day, it is anticipated that the usage amount of the reagent of the target arithmetic processing day will probably exceed the average usage amount of the reagent. In this case, the difference between the usage amount of the reagent of the target arithmetic processing day and the average usage amount of the reagent can be considered as an increase, included in the usage amount of the reagent of the target arithmetic processing day, caused by the fact that the preceding day is an irregular holiday. Moreover, as described above, when there are a plurality of consecutive irregular holidays immediately before the target arithmetic processing day, the usage amount of the reagent of the target arithmetic processing day increases in accordance with the number of consecutive irregular holidays. In the present embodiment, it is considered that the usage amount of the reagent of the target arithmetic processing day increases in proportion to the number of consecutive irregular holidays. Therefore, the difference (the increased amount in the usage amount of the reagent) between the usage amount of the reagent of the target arithmetic processing day and the average usage amount of the reagent is divided by the second number-of-consecutive-holidays (the number of consecutive irregular holidays immediately before the target arithmetic processing day), and the obtained result is set as the provisional addition component. That is, the provisional addition component corresponds to the increased amount included in the usage amount of the reagent per irregular holiday.

Next, the CPU 401 determines whether the addition component is greater than "0" (step S634). Since the initial value of the addition component is "0", the addition component greater than "0" means that the addition component has been at least changed from the initial value. When the addition component is greater than "0" (YES in step S634), the CPU 401 sets, as a new addition component, a result obtained by dividing by 2 the sum of the addition component and the provisional addition component, that is, the average value of the addition component and the provisional addition component (step S635). On the other hand, when the addition component is less than or equal to "0" (NO in step S634), the CPU 401 sets the value of the provisional addition component as the addition component (step S636). After setting the addition component in step S635 or step S636, the CPU 401 returns the process to the address for calling the addition component calculation process in the addition component determination process.

When the second number-of-consecutive-holidays is less than or equal to "0" in step S631, that is, there is no irregular holiday immediately before the target arithmetic processing day (NO in step S631), the CPU 401 returns the process to the address for calling the addition component calculation process in the addition component determination process, without performing the arithmetic processing regarding the addition component. At this time, since the arithmetic processing regarding the addition component is not substantially performed, the value of the arithmetic processing execution flag is not changed. That is, when the arithmetic processing execution flag is "0", "0" is maintained, and when the arithmetic processing execution flag is "1", "1" is maintained.

When the addition component calculation process as described above ends, the CPU 401 increments by 1 the parameter "the number of days to add" (step S608). Further, the CPU 401 determines whether a predetermined ending condition is satisfied (step S609). The ending condition here is that the number of days to add is greater than 50 or that no usage amount of the reagent before the target arithmetic processing day is registered in the reagent usage history database DB200. Here, when the ending condition is not satisfied, that is, when the number of days to add is smaller than 50 and there is a usage amount of the reagent before the target arithmetic processing day registered in the reagent usage history database DB200 (NO in step S609), the CPU 401 selects a day, in the preceding week of the arithmetic processing day, that falls on the same day of the week as the target arithmetic processing day, as a new target arithmetic processing day (step S610), and returns the process to step S605.

On the other hand, when the ending condition is satisfied in step S608, that is, when the number of days to add is greater than 50, or when no usage amount of the reagent before the target arithmetic processing day is registered in the reagent usage history database DB200 (YES in step S609), the CPU 401 performs an addition component adjustment process (step S611).

Figure 18:
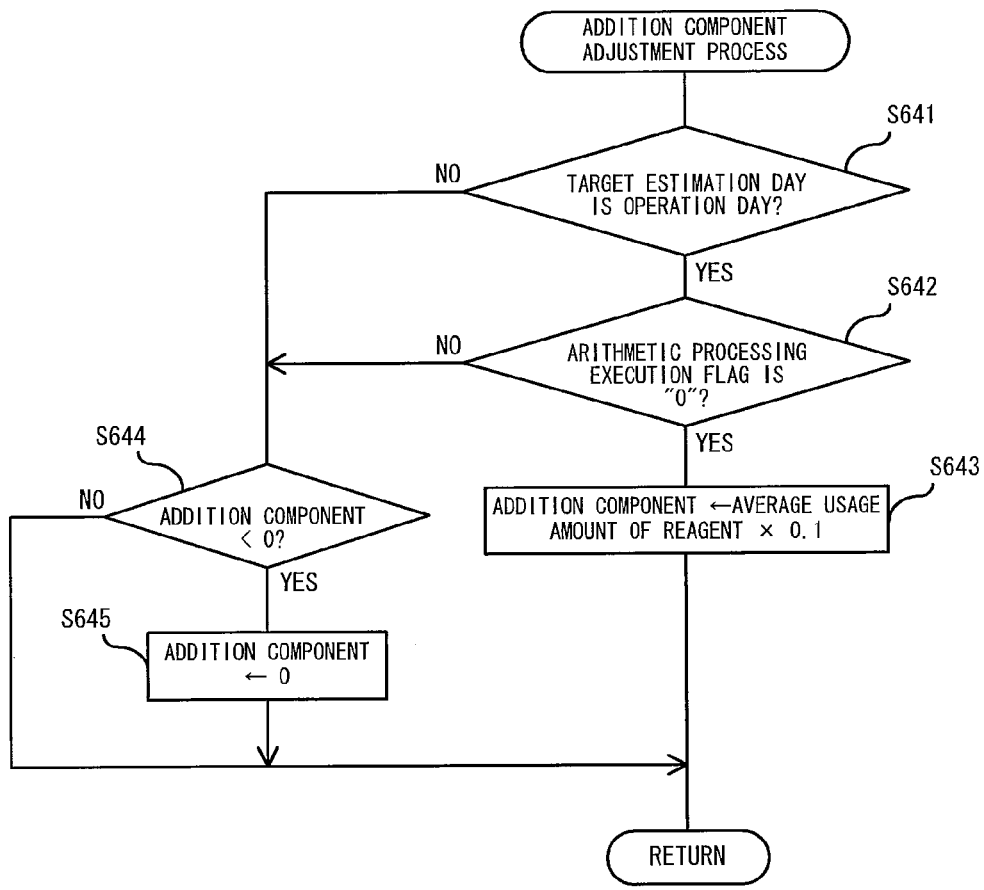
FIG. 18 is a flow chart showing the flow of an addition component adjustment process.

FIG. 18 is a flow chart showing the flow of the addition component adjustment process. First, the CPU 401 determines whether the target estimation day is an operation day (step S641). This process is a process similar to that of step S403, and uses the operation day table OPT.

When the target estimation day is an operation day in step S641 (YES in step S641), the CPU 401 determines whether the arithmetic processing execution flag is set to "0", that is, the above-described arithmetic processing has never been performed (step S642). When the arithmetic processing execution flag is set to "0" (YES in step S642), it means that although the target estimation day is an operation day, the arithmetic processing regarding the addition component has never been performed in the addition component calculation process (that is, the value of the parameter "addition component" is "0"). In this case, the CPU 401 sets the parameter "addition component" to a result obtained by multiplying the average usage amount of the reagent by 0.1, that is, a value of one tenth of the average usage amount of the reagent (step S643), and returns the process to the address for calling the addition component adjustment process in the reagent usage amount estimation process.

On the other hand, when the target estimation day is a non-operation day in step S641 (NO in step S641), or when the arithmetic processing execution flag is set to "1" in step S642 (that is, the arithmetic processing regarding the addition component has been performed at least once) (NO in step S642), the CPU 401 determines whether the value of the parameter "addition component" is less than 0 (step S644). When the value of the parameter "addition component" is less than 0, that is, the value of the parameter "addition component" is a negative number (YES in step S644), the CPU 401 sets the parameter "addition component" to 0, determining the value of the addition component as inappropriate (step S645). Thereafter, the CPU 401 returns the process to the address for calling the addition component adjustment process in the reagent usage amount estimation process.

When the value of the parameter "addition component" is greater than or equal to 0 in step S644 (NO in step S644), the CPU 401 returns the process to the address for calling the addition component adjustment process in the reagent usage amount estimation process, without changing the value of the parameter "addition component".

When the addition component adjustment process as described above ends, the CPU 401 determines whether all measurement items have been set as target measurement items (step S612). When there are measurement items remaining that have not been set as target measurement items (NO in step S612), the CPU 401 sets one of the remaining measurement items as a target measurement item (step S613), and returns the process to step S602.

On the other hand, when all measurement items have been set as target measurement items in step S612 (YES in step S612), the CPU 401 returns the process to the address for calling the addition component determination process in the reagent usage amount estimation process.

Figure 19:
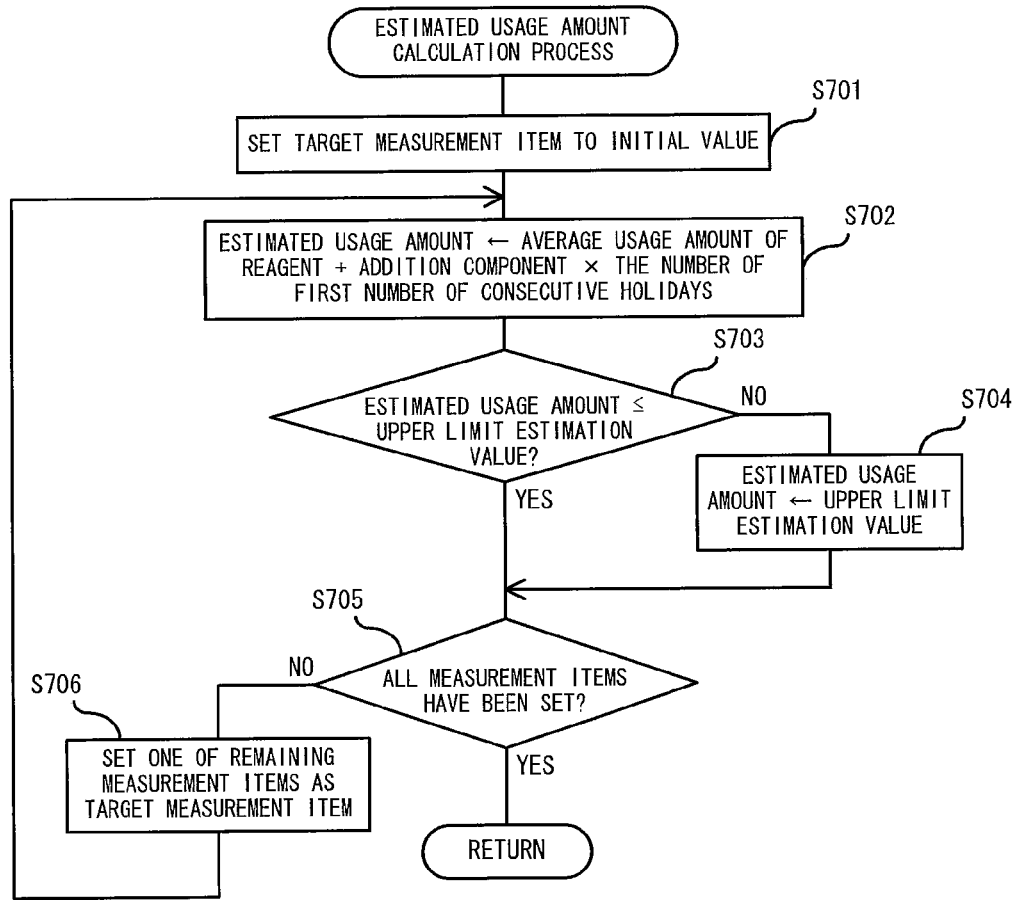
FIG. 19 is a flow chart showing the flow of an estimated usage amount calculation process.

After ending the addition component determination process described above, the CPU 401 performs the estimated usage amount calculation process (step S205). FIG. 19 is a flow chart showing the flow of the estimated usage amount calculation process.

First, the CPU 401 sets the target measurement item for which an addition component is to be calculated to an initial value (step S701). This initial value is the same as the initial value used for the measurement item in steps S301, S401, and S601.

Next, the CPU 401 determines the sum of: a result obtained by multiplying the first number-of-consecutive-holidays (that is, the number of consecutive irregular holidays immediately before the target estimation day) by the addition component; and the average usage amount of the reagent. Then, the CPU 401 sets this sum as an estimated usage amount of the reagent (step S702). In other words, in this process, the estimated usage amount of the reagent is calculated by correcting the average usage amount of the reagent in accordance with the number of consecutive irregular holidays immediately before the target estimation day.

Next, the CPU 401 determines whether the estimated usage amount is greater than or equal to a predetermined upper limit estimation value (step S703). The upper limit estimation value is a numerical value provided in advance, and represents an upper limit for an estimated value of the usage amount of the reagent. When the estimated usage amount is greater than or equal to the upper limit estimation value in step S703 (YES in step S703), the CPU 401 sets the estimated usage amount to the upper limit estimation value (step S704). Accordingly, when the estimated usage amount is excessively large, the estimated usage amount is corrected to the upper limit estimation value. Thereafter, the CPU 401 returns the process to step S705.

When the estimated usage amount is less than the upper limit estimation value in step S703 (NO in step S703), the CPU 401 advances the process to step S705, without correcting the estimated usage amount.

In step S705, the CPU 401 determines whether all measurement items have been set as target measurement items (step S705). When there are measurement items remaining that have not been set as target measurement items (NO in step S705), the CPU 401 sets one of the remaining measurement items as a target measurement item (step S706), and returns the process to step S702.

When all measurement items have been set as target measurement items in step S705 (YES in step S705), the CPU 401 returns the process to the address for calling the estimated usage amount calculation process in the reagent usage amount estimation process.

After ending the estimated usage amount calculation process, the CPU 401 returns the process to the address for calling the reagent usage amount estimation process in the main routine.

Immediately after the sample analyzer 1 is activated, the estimation of the usage amount of the reagent as described above is performed with the current day set as the target estimation day. However, depending on the facility where the sample analyzer 1 is installed, the sample analyzer 1 may be caused to operate still after the date is changed, such as in a case where the sample analyzer 1 is caused to operate during night. In this case, associated with the change of the date, the estimation of the usage amount of the reagent is performed again.

Figure 20:
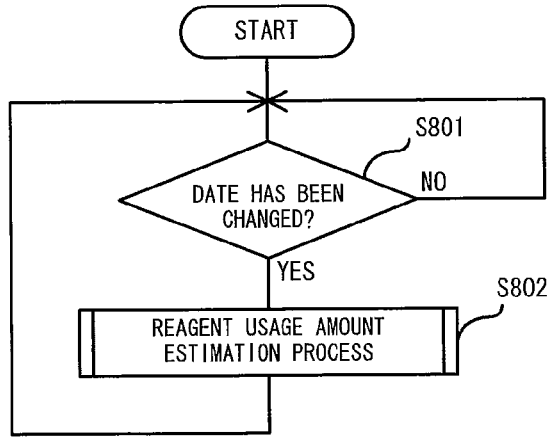
FIG. 20 is a flow chart showing the flow of operations performed by a sample analyzer when an estimation of a usage amount of a reagent is performed after the date has been changed.

FIG. 20 is a flow chart showing the flow of operations performed by the sample analyzer 1 when the estimation of the usage amount of the reagent is performed associated with the change of the date. The CPU 401 of the information processing apparatus 4 determines whether the date has been changed (step S801). Since the date is changed at 0:00 a.m., it is usually determined that the date has been changed when it has become 0:00 a.m. However, some facilities employ a rule to change the date at a time other than 0:00 a.m. In such a case, by determining whether it has become the time when the date is to be changed at that facility (the facility where the sample analyzer 1 is installed), it is determined whether the date has been changed. The CPU 401 repeats the process of step S801 until the date is changed (NO in step S801).

When it is determined that the date has been changed in step S801 (YES in step S801), the CPU 201 performs the reagent usage amount estimation process for the new date (step S802). That is, the CPU 401 performs the reagent usage amount estimation process again, with the new date set as the target estimation day. When the reagent usage amount estimation process ends, the CPU 401 returns the process to step S801.

In this manner, when the date is changed after an estimated usage amount of the reagent was already calculated, the estimated usage amount of the reagent is updated to an estimated usage amount of the new date. Accordingly, it is possible to prevent the estimated usage amount of the previous day from being continued to be used after the date has been changed.

Meanwhile, in the sample analyzer 1, the result of the estimation of the usage amount of the reagent can be displayed. The estimation result of the usage amount of the reagent is displayed on the maintenance status confirmation screen. The maintenance status confirmation screen is displayed as an initial screen after the log-on, as described above, and is also displayed by being called from another screen through an operation by the user, as described below.

Figure 21:
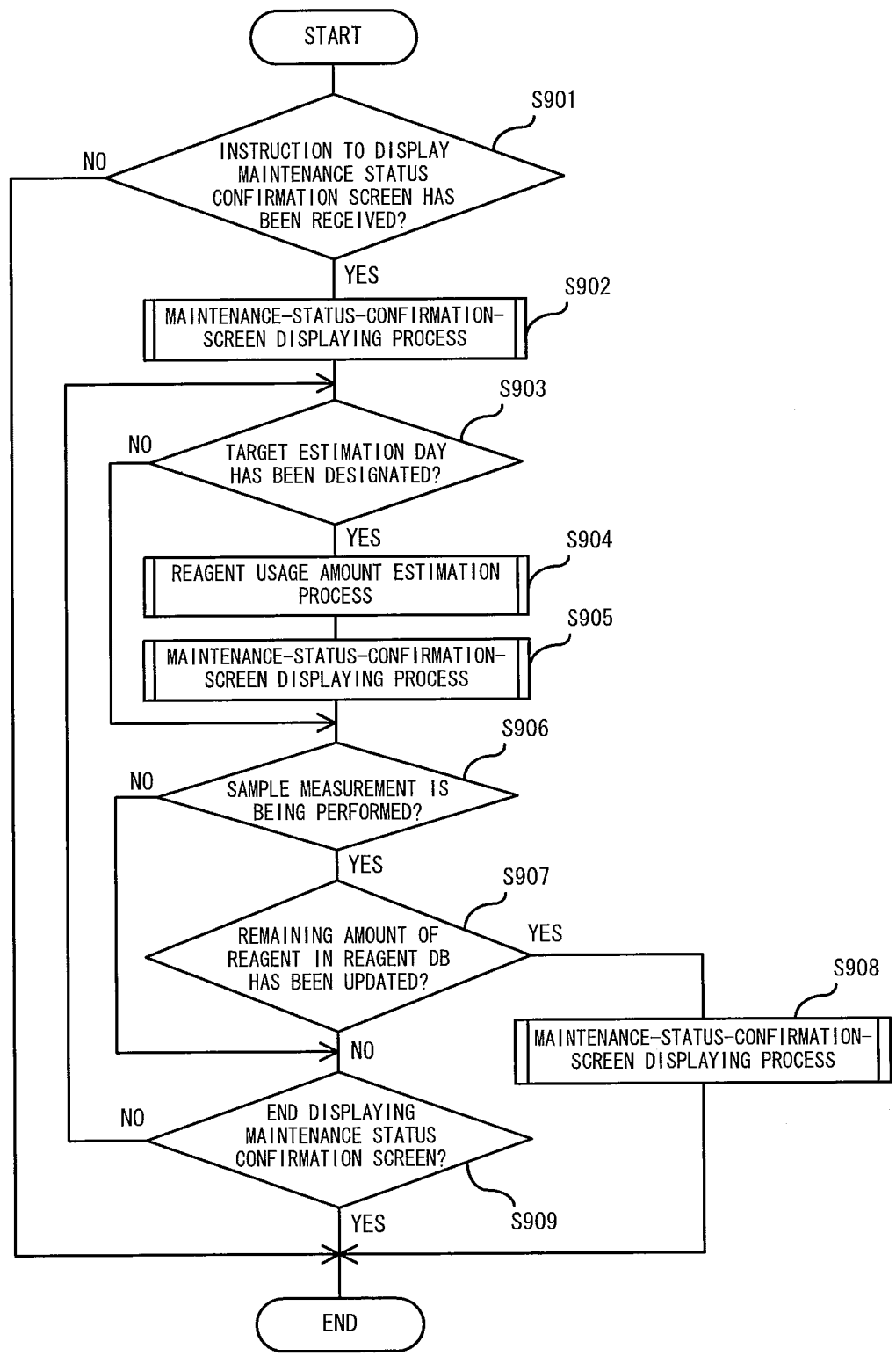
FIG. 21 is a flow chart showing the flow of operations performed by a sample analyzer when a result of an estimation of a usage amount of the reagent is to be displayed.

FIG. 21 is a flow chart showing the flow of operations performed by the sample analyzer when a result of an estimation of the usage amount of the reagent is to be displayed. By operating the input unit 410, the user can instruct the information processing apparatus 4 to display the maintenance status confirmation screen. The CPU 401 determines whether it has received the instruction to display the maintenance status confirmation screen (step S901), and when the CPU 401 has not received the instruction to display the maintenance status confirmation screen (NO in step S901), the CPU 401 ends the process.

On the other hand, when the CPU 401 has received the instruction to display the maintenance status confirmation screen in step S901 (YES in step S901), the CPU 401 performs the maintenance-status-confirmation-screen displaying process (step S902).

Figure 22:
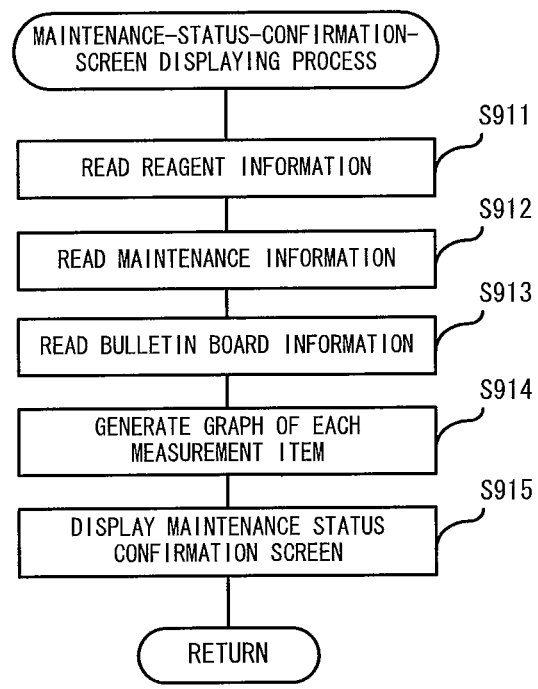
FIG. 22 is a flow chart showing the steps of a maintenance-status-confirmation-screen displaying process.

FIG. 22 is a flow chart showing the steps of the maintenance-status-confirmation-screen displaying process. In the maintenance-status-confirmation-screen displaying process, the CPU 401 obtains reagent information first (step S911). In this process, reagent management information is read form the reagent DB, and a result of the estimation performed in the reagent usage amount estimation process is read from the hard disk 404 or the RAM 403.

Next, the CPU 401 reads maintenance information from the maintenance information DB (step S912). The maintenance information to be read here is information of a maintenance operation to be performed on the current day (a designated target day).

Next, the CPU 401 obtains bulletin board information from the bulletin board DB (user names and messages of contributors) (step S913).

Next, based on the read reagent information in step S912, the CPU 401 generates a graph regarding a remaining amount of a reagent for each measurement item (step S914). This process will be described further in detail. As described below, a graph regarding a remaining amount of a reagent for each measurement item is displayed on the maintenance status confirmation screen. Each graph regarding a remaining amount of a reagent includes a graph (bar) indicating a remaining amount of the reagent, a bar graph (bar) indicating an estimated usage amount of the reagent, and a bar graph indicating a shortage amount of the reagent. In step S914, the CPU 401 generates these graphs for each measurement item.

After generating the graphs for each measurement item, the CPU 401 causes the display unit 420 to display the maintenance status confirmation screen (step S915), and returns the process to the address for calling the maintenance-status-confirmation-screen displaying process in the main routine.

FIG. 23 is a diagram showing an example of the maintenance status confirmation screen. The maintenance status confirmation screen DP is provided with a reagent information area A100 for displaying results of estimations of usage amounts of reagents. In the reagent information area A100, information of a remaining amount, an estimated usage amount, and an excess or shortage of a reagent are displayed for each measurement item. The reagent information area A100 is a table area composed of a plurality of lines, and each line corresponds to a measurement item. The reagent information area A100 is divided into two columns. On the left column, the name of a measurement item is displayed in each line. On the right column, numerical information C101 indicating a remaining amount of a corresponding reagent, numerical information C102 indicating an excess or shortage amount of the reagent, and graphic information G103 indicating the relationship between the remaining amount, an estimated usage amount, and the excess or shortage amount of the reagent are displayed in each line. The graphic information G103 includes a horizontally-elongated bar G104 indicating a remaining amount of the reagent. The bar G104 is green, and the magnitude of the remaining amount corresponds to the length of the bar. That is, the more the remaining amount is, the longer the bar G104 is, and the less the remaining amount is, the shorter the bar G104 is. The bar G104 is displayed so as to extend rightward from the left end thereof (hereinafter referred to as "reference position"). That is, the reference position of the area where the bar G104 can be displayed corresponds to a state where the remaining amount of the reagent is "0", and the right end position of the area (hereinafter referred to as "upper limit position") corresponds to a state where the reagent container is full. When the remaining amount of the reagent is "0", the bar G104 is not displayed, and when the reagent container is full, the bar G104 is displayed from the reference position to the upper limit position in the area. For example, when the remaining amount of the reagent is 70%, the bar G104 having a length corresponding to 70% of the length from the reference position to the upper limit position is displayed, extending rightward from the reference position. Accordingly, only by confirming the length of the bar G104, the user can intuitively discern an approximate remaining amount of the reagent.

Figure 24:
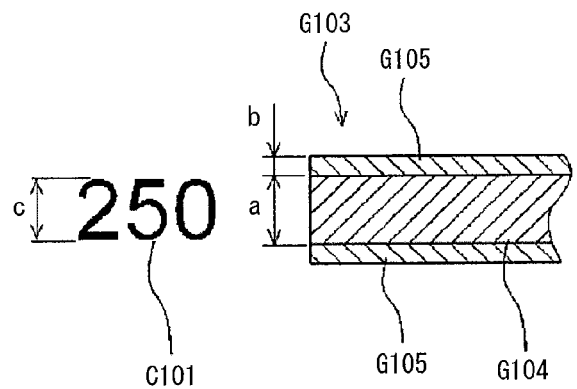
FIG. 24 is a diagram for describing the dimensions of numerical information of a remaining amount of a reagent, a graph showing the remaining amount of the reagent, and a graph showing an estimated usage amount of the reagent.

Bars G105 each indicating the estimated usage amount of the reagent are displayed on the upper and lower sides of the bar G104, respectively, and in parallel to the bar G104. Each bar G105 is gray, and has a narrower width than the bar G104. FIG. 24 is a diagram for describing the dimensions of the numerical information C101, the bar G104, and the bars G105. Specifically, the ratio of the thickness a of the bar G104 to the thickness b of one bar G105 is about 4:1. Moreover, the thicknesses of the bars G105 sandwiching the bar G104 are identical to each other. Each bar G105 can be displayed in a range from the reference position to the upper limit position, and the magnitude of the estimated usage amount corresponds to the length thereof. That is, the more the estimated usage amount is, the longer the bar G105 is, and the less the estimated usage amount is, the shorter the bar G105 is. The bar G105 is displayed so as to extend rightward from the reference position. That is, when the estimated usage amount is "0", the bar G105 is not displayed, and when the estimated usage amount is the full amount of the reagent container, the bar G105 is displayed from the reference position to the upper limit position. For example, when the estimated usage amount of the reagent is 70% of the full amount of the reagent container, the bar G105 having a length corresponding to 70% of the length from the reference position to the upper limit position is displayed, extending rightward from the reference position. Accordingly, only by confirming the length of the bar G105, the user can intuitively discern an approximate estimated usage amount of the reagent.

Moreover, since the bar G104 and the bars G105 are displayed in parallel and adjacent to each other, and since they are displayed so as to extend rightward from the identical reference position in accordance with their volumes, the user can easily compare the current remaining amount of the reagent and the estimated usage amount. In addition, each bar G105 is thinner than the bar G104. The bar G104 is green, which is a chromatic color, whereas the bar G105 is gray, which is an achromatic color. Accordingly, the user can easily distinguish the bar G104 from the bars G105. Further, by making the bar G104 thicker than each bar G105, the bar G104 can be made more conspicuous than the bars G105. Further, the bar G104 (the remaining amount of the reagent) is displayed in a bright, conspicuous color, and each bar G105 (the estimated usage amount of the reagent) is displayed in a somber color. Accordingly, the remaining amount of the reagent, which is more important information, can be made conspicuous than the estimated usage amount of the reagent.

A difference between the remaining amount of the reagent and the estimated usage amount is displayed as an excess or shortage amount C102. Specifically, when the remaining amount of the reagent exceeds the estimated usage amount, an excessive amount of the reagent, that is, a remaining amount of the reagent at a time when the entire estimated usage amount has been consumed, is displayed as the excess or shortage amount C102. In this case, the bar G104 indicating the remaining amount of the reagent is longer than the bars G105 each indicating the estimated usage amount, and thus, the bar G104 projects rightward from the right ends of the bars G105. This projecting amount corresponds to the excessive amount of the reagent. On the other hand, when the estimated usage amount exceeds the remaining amount of the reagent, a shortage amount of the reagent, that is, an amount of the reagent that will be further required on the day when all of the remaining amount of the reagent is consumed, is displayed as the excess or shortage amount C102. In this case, the bars G105 each indicating the estimated usage amount is longer than the bar G104 indicating the remaining amount of the reagent, and thus, the bars G105 project rightward from the right end of the bar G104. This projecting amount corresponds to the shortage amount of the reagent. The shortage amount is displayed by a bar G106, which is red. That is, the bar G106 indicating the shortage amount is displayed adjacent to the right end of the bar G104 indicating the remaining amount of the reagent, so as to extend from the right end of the bar G104 indicating the remaining amount of the reagent to the right ends of the bars G105 each indicating the estimated usage amount. For example, when the remaining amount of the reagent is 60% of the full volume of the reagent container, and the estimated usage amount is the full volume of the reagent container, the bar G104 having a length corresponding to 60% of the length from the reference position to the upper limit position is displayed, extending rightward from the reference position, and the bars G105 are displayed from the reference position to the upper limit position. At this time, the bar G106 is displayed from the right end of the bar G104 to the right ends of the bars G105 (see the measurement item "HBsAb" in FIG. 23). When the remaining amount of the reagent is "0" and the estimated usage amount is the full volume of the reagent container, the bar G106 indicating the shortage amount is displayed in the full range from the reference position to the upper limit position (see the measurement item "FT3" in FIG. 23). Further, when the remaining amount of the reagent is "0" and the estimated usage amount is 5% of the full volume of the reagent container, the bar G106 having a length corresponding to 5% of the length from the reference position to the upper limit position is displayed, extending rightward from the reference position (see the measurement item "TestA" in FIG. 23). Accordingly, the relationship between the remaining amount and the estimated usage amount of the reagent, such as, whether the remaining amount of the reagent exceeds or falls behind the estimated usage amount, and approximately how much excessive or in short the reagent is, can be easily discerned.

Further, the bar G104 is green, and the bar G106 is red. Since the bar G104 indicating the remaining amount of a reagent and the bar G106 indicating the shortage amount of the reagent are displayed in colors having different hues from each other, the user can easily distinguish the bar G104 from the bar G106. Further, the bar G104 indicating the remaining amount of a reagent is displayed in green, which indicates "go" in the case of a traffic light, and the bar G106 indicating the shortage amount of the reagent is displayed in red, which indicates "stop" in the case of a traffic light. The bar G104 indicates the remaining amount of the reagent and shows that sample measurements can be performed by the remaining amount. By displaying the bar G104 in green which indicates "go" in a traffic light, it is possible to cause the user to imagine that sample measurements can be performed by the amount indicated by the bar G104. On the other hand, the bar G106 indicates the shortage amount of the reagent, and shows that sample measurements that correspond to that shortage amount cannot be performed. By displaying the bar G106 in red which indicates "stop" in the case of a traffic light, it is possible to cause the user to imagine that sample measurements corresponding to that amount indicated by the bar G106 cannot be performed.

The thickness of the bar G106 is the same as that of the bar G104. Therefore, the bar G106 is thicker than each bar G105. In addition, the bar G106 is red, which is a chromatic color, and each bar G105 is gray, which is an achromatic color. Accordingly, the user can easily distinguish the bar G106 from the bars G105. Further, by making the bar G106 thicker than each bar G105, the bar G106 can be made more conspicuous than the bar G105. Further, the bar G106 (the shortage amount of a reagent) is displayed in a bright, conspicuous color, and the bar G105 (the estimated usage amount of the reagent) is displayed in a somber color. Accordingly, the shortage amount of a reagent, which is more important information, can be made more conspicuous than the estimated usage amount of the reagent.

Further, two bars G105 are arranged so as to sandwich the bar G104 and the bar G106. The right end of each of the two bars G105 indicates the estimated usage amount of the reagent. When the bar G104 is shorter than the bars G105, the right ends of the bars G105 coincide with the right end of the bar G106, and the positions of the right ends of the bars G105, that is, the estimated usage amount of the reagent, can be easily understood. On the other hand, when the bar G104 is longer than the bars G105, the bar G104 projects rightward from the right ends of the bars G105. Also in this case, by providing the bars G105 indicating the estimated usage amount of the reagent in parallel to each other, the user observing the graphic information G103 can imagine an imaginary line that connects the right ends of the two bars G105, although the two bars G105 are located, separated from each other. Thus, such an imaginary line allows the user to easily discern the estimated usage amount of the reagent.

Moreover, the reagent information area A100 is provided with a plurality of lines, and information of a reagent is displayed in each line. In each line, the name of a measurement item, the numerical information C101 indicating the remaining amount of a reagent, the graphic information G103, and the numerical information C102 indicating an excess or shortage amount of the reagent are displayed. The name of a measurement item, and the numerical information C101 and C102 are text information (character information), and are displayed in one level and not displayed in stacks in vertical directions. Moreover, the thickness a of each of the bars G104 and G106 is slightly larger than the height c of each character of the text information. Specifically, as shown in FIG. 24, the ratio of the thickness a of the bar G104 to the height c of each character of the numerical information C101 is about 10:9. Moreover, the thickness a+2b, which is obtained by adding up the thickness of the bar G104 and the thicknesses of the bars G105 (that is, the entire thickness of the graphic information G103), is slightly larger than the height c of each character of the text information. Specifically, the ratio of a+2b to c is about 5:3. It should be noted that the character sizes used for the name of a measurement item and the numerical information C101 and C102 displayed in the reagent information area A100 are all 10 point.

As described above, in the reagent information area A100, the character information per line is all displayed in one level, and the thickness (height) of the graphic information G103 is smaller than twice of the height of each character of the character information. That is, an area having the height (a+2b), which is slightly larger than the character height c (that is, an area having a height larger than that of one line of text information and smaller than the height of two lines of text information), contains all information regarding the remaining amount of a reagent used for one measurement item (the name of the measurement item, the numerical information C101 indicating a remaining amount of the reagent, the graphic information G103, and the numerical information C102 indicating an excess or shortage amount of the reagent). In general, in order to display text information in one line, it is necessary to provide margin areas in upper and lower sides of the text information, respectively, each margin area having a height from about a half of the character height to the height of one line. As described above, the ratio of the height a+2b of the graphic information G103 to the height c of the character information C101 and C102 is about 5:3, and the height of the graphic information G103 coincides with the height obtained by combining the height of one line of text information and the heights of general margin areas. Therefore, it is possible to display, in the area that can display one line of text information, not only the name of a measurement item, the numerical information C101 indicating the remaining amount of a reagent, the numerical information C102 indicating an excess or shortage amount of the reagent, but also the graphic information G103. Since the height of the graphic information G103 is smaller than twice of the character height of the text information as described above, displaying the graphic information G103 does not require a height of two or more lines of text information. Thus, in the reagent information area A100, the area corresponding to one line of text information can contain all information regarding the remaining amount of a reagent used for one measurement item (the name of the measurement item, the numerical information C101 indicating a remaining amount of a reagent, the graphic information G103, and the numerical information C102 indicating an excess or shortage amount of the reagent). As a result, information of remaining amounts of reagents for many measurement items can be displayed in the reagent information area A100.

Moreover, in the present embodiment, the character height c of the text information is 10 point, and this corresponds to 13.33 pixels (dots) in the case of a standard screen resolution 96 dpi. The thickness a of the bars G104 and G106 is slightly larger than the character height c of the text information, and corresponds to about 15 pixels in the above resolution. Accordingly, the user can view the bars G104 and G106 on the screen well. Further, the thickness of one bar G105 is about 3 to 4 pixels. Since a line of 3 to 4 pixels would be easily viewed, sufficient visibility of the bar G105 is secured.

In an upper part of the reagent information area A100, a date designation icon B200 is displayed. The date designation icon B200 is a graphical object (control) that can be selected by means of a mouse operation or the like, and when the date designation icon B200 is selected, a date designation calendar is displayed. By the user selecting a desired date from this calendar, the date can be designated as a target estimation day. It should be noted that the range in which a target estimation day can be designated in this calendar is from the current day to the fifth day from the current day.

To the left of the reagent information area A100, a consumables information area A300 for displaying information of consumables other than reagents is provided. Information of the remaining number of cuvettes in the cuvette feeder 10, and information of the remaining number of pipette tips in the pipette tip feeder 13 are displayed in the consumables information area A300. The information of the remaining number of cuvettes is displayed as an icon B301, and the information of the remaining number of pipette tips is displayed as an icon B302. That is, when the remaining number of cuvettes is enough, the icon B301 is displayed in green, and when the remaining number of cuvettes is not enough, the icon B301 is displayed in red. Similarly, the remaining number of pipette tips is enough, the icon B302 is displayed in green, and when the remaining number of pipette tips is not enough, the icon B302 is displayed in red.

To the left of the consumables information area A300, an operation information area A400 for displaying a list of operations that should be performed on the day is provided. In the operation information area A400, the names of operations (To Do) that the user should do on the day are listed. This operation information can be set by a user from another setting screen. A check-mark icon B401 is displayed next to an operation that has been performed. Moreover, the user name of the user who performed the operation is displayed to the right of the operation name ("auto" is displayed when the operation was automatically executed by the sample analyzer 1). The time at which the operation was performed is displayed to the right thereof. For an operation that has not been performed, a user name is not displayed. For an operation that has not been performed, the time at which the operation is performed is not usually displayed. However, for an operation for which automatic execution is scheduled at a predetermined time, the scheduled time is displayed in parentheses.

Accordingly, the user can easily confirm operations that the user should do on the day, which operation, among the operations that the user should do, was already performed, who performed the operation, and when the operation was performed.

A bulletin board area A500 for displaying messages between users is provided below the operation information area A400. Messages from other users are listed in the bulletin board area A500. Such a message can be inputted by a user through another input screen. The user name of the user who inputted the message and the input time are displayed to the right of the message. Accordingly, users can easily communicate with each other, not through direct conversation. Only by confirming the content of the bulletin board area A500, the user can easily know who inputted what message.

The maintenance status confirmation screen DP as described above is usually displayed before a user starts operations of the day, after the sample analyzer 1 has been activated. On the maintenance status confirmation screen DP, not only estimated usage amounts of reagents to be used for the day, but also all matters that the user should prepare for starting operations of the day are displayed. Therefore, only by confirming the maintenance status confirmation screen DP, the user can smoothly prepare for the operation to be started. Moreover, information of estimated usage amounts and excess or shortage amounts of reagents based on the estimated usage amounts is displayed on the maintenance status confirmation screen DP. Therefore, the user can easily confirm a reagent for which shortage is anticipated, and can smoothly perform the operations of the day by adding, replacing, or ordering the reagent.

With reference back to FIG. 21, operations for displaying a result of an estimation of a usage amount of a reagent will be described. As described above, the user can designate a target estimation day other than the current day, by operating the date designation icon B200. The CPU 401 determines whether the designation of the target estimation day has been received (step S903), and when the designation of the target estimation day has been received (YES in step S903), the CPU 401 perform the reagent usage amount estimation process described above for the designated target estimation day (step S904). After ending the reagent usage amount estimation process, the CPU 401 performs the maintenance-status-confirmation-screen displaying process, based on the obtained results of the estimations of the usage amounts of reagents (step S905). Accordingly, the maintenance status confirmation screen is updated.

When the designation of the target estimation day has not been received in step S903 (NO in step S903), or when the maintenance status confirmation screen has been updated in step S905, the CPU 401 determines whether a sample measurement is being performed by the sample analyzer 1 (step S906). When no sample measurement is being performed (NO in step S906), the CPU 401 advances the process to step S909. On the other hand, when a sample measurement is being performed by the sample analyzer 1 (YES in step S906), the CPU 401 determines whether the remaining amount of each reagent has been updated in the reagent DB as a result of the reagent having been used in the sample measurement (step S907). When the remaining amount of the reagent has not been updated (NO in step S907), the CPU 401 advances the process to step S909. On the other hand, when the remaining amount of the reagent in the reagent DB has been updated (YES in step S907), the estimated usage amount of the reagent has also been updated in association with the update of the remaining amount thereof (see step S106 in FIG. 6). In this case, the CPU 401 performs the maintenance-status-confirmation-screen displaying process based on the updated remaining amount of the reagent and the updated estimated usage amount of the reagent (step S908). As a result, the maintenance status confirmation screen is updated.

The user can instruct the sample analyzer 1 to switch the display from the maintenance status confirmation screen to another screen by operating the input unit 420. The display of the maintenance status confirmation screen ends upon being switched to another screen. In step S909, the CPU 401 determines whether an instruction to end displaying the maintenance status confirmation screen (that is, an instruction to switch the display to another screen) has been received (step S909). When the instruction to end displaying the maintenance status confirmation screen has not been received (NO in step S909), the CPU 401 returns the process to step S903. On the other hand, when the instruction to end displaying the maintenance status confirmation screen has been received (YES in step S909), the CPU 401 ends the process.

As described above, in the sample analyzer 1 according to the present embodiment, a remaining amount of a reagent and an estimated usage amount of the reagent is graphically displayed in a bar graph. Therefore, the user can intuitively discern the remaining amount of the reagent and the estimated usage amount. Moreover, since a numerical value of the remaining amount of the reagent and a numerical value of the estimated usage amount are also displayed, the user can easily discern the necessary refill amount of the reagent.

Moreover, in the sample analyzer 1 according to the present embodiment, the width of the bar G104 is different from the width of each bar G105. Accordingly, the user can easily distinguish the bar G104 from the bars G105, and thus, the user can easily discern the necessary refill amount of the reagent.

Moreover, in the sample analyzer 1 according to the present embodiment, the bar G106 is displayed so as to be continuous to an end of the bar G104. Accordingly, only a small width (height) is necessary for displaying the bar G104 and the bar G106, and thus, much information can be efficiently displayed.

Moreover, in the sample analyzer 1 according to the present embodiment, usage amount information that is to be used in arithmetic processing, among usage amount information stored in the reagent usage history database DB200, is determined based on a result of determination whether a past date is a holiday, and a usage amount of the reagent is estimated based on the determined usage amount information. Therefore, it is possible to more accurately estimate the usage amount of the reagent of the target estimation day, than in a conventional sample analyzer. For example, when the target estimation day is Monday, it is possible to extract only the usage amount of the reagent of an operation day, from among data of Mondays in the reagent usage history database DB200, and calculate an estimated usage amount. Accordingly, since data of a Monday that falls on, for example, a public holiday is not reflected in the estimated usage amount, it is possible to more accurately estimate the usage amount of the reagent of the target estimation day.

Moreover, in the sample analyzer 1 according to the present embodiment, when the preceding day of the target estimation day is a holiday, an addition component is accordingly added to the usage amount of the reagent of the target estimation day. Therefore, it is possible to more accurately estimate the usage amount of the reagent of the target estimation day, by reflecting the fact that the target estimation day is a following day of a holiday.

Other Embodiments

In the above embodiment, a configuration has been described in which a usage amount of a reagent, as an example of a consumable, is estimated. However, the present invention is not limited thereto. As long as a consumable is used in a sample analysis, a usage amount of a consumable other than a reagent may be estimated. For example, the usage number of cuvettes may be estimated, or the usage number of pipette tips may be estimated. In the case of a consumable which is consumed one by one every time one sample measurement is performed as in the cases of cuvettes and pipette tips, the number of the consumed articles coincides with the number of measurements performed, as in the case of a reagent. Therefore, it is possible to calculate an estimated usage number of consumables by use of a process similar to the above-described estimation process of a consumption amount of a reagent.

Further, in the above embodiment, a configuration has been described where: the ratio of the thickness (height) of the bar G104 to the thickness (height) of each bar G105 is 4:1, the bar G104 being a graph indicating a remaining amount of a reagent, the bar G105 being a graph indicating an estimated usage amount of the reagent, both displayed on the maintenance status confirmation screen; and the two bars G105 are located adjacent to the upper end and the lower end of the bar G104, respectively. However, the present invention is not limited thereto. As long as each bar G105 is thinner than the bar G104, the above described ratio need not be satisfied. For example, the ratio of the thickness of the bar G104 to the thickness of each bar G105 may be 2:1, or 5:3. In such a case, although the total thickness of the two bars G105 becomes greater than or equal to the thickness of the bar G104, such a configuration is not excluded. Still alternatively, as long as the bar G104 and the bars G105 are located next to each other, they may be located, separated from each other.

In the above embodiment, the bar G104 is green, the bars G105 are gray, and the bar G106 is red. However, the present invention is not limited thereto. Each bar G105 may be white or a black, which is an achromatic color, as long as white or black is a color different from that of the background. Still alternatively, each bar G105 may be a chromatic color. In this case, by making the degree of chroma of the bars G105 lower than that of the bar G104, the bar G104 can be made more conspicuous than the bars G105. Similarly, by making the degree of chroma of the bars G105 lower than that of the bar G106, the bar G106 can be made more conspicuous than the bars G105.

Further, a chromatic color other than green may be used for the bar G104, and a chromatic color other than red may be used for the bar G106. In this case, it is necessary that the color of the bar G104 and the color of the bar G106 are different from each other.

Further, in the above embodiment, the ratio of the height a+2b of the graphic information G103 to the height c of each character of the name of a measurement item, of the numerical information C101 indicating a remaining amount of a reagent, and of the numerical information C102 indicating an excess or shortage amount of the reagent, is set about 5:3. However, the present invention is not limited thereto. Although the relationship between the character height of text information and the height of graphic information may be freely set, it is preferable that the height of graphic information is greater than the character height of text information and is less than twice of the character height. Then, an area less than two lines of text information can contain all information regarding the remaining amount of a reagent, including graphic information. Further, the character size of text information may not be 10 point. The character size of text information is preferably 9 point to 15 point, which are used in a standard screen display.

Figure 25A:
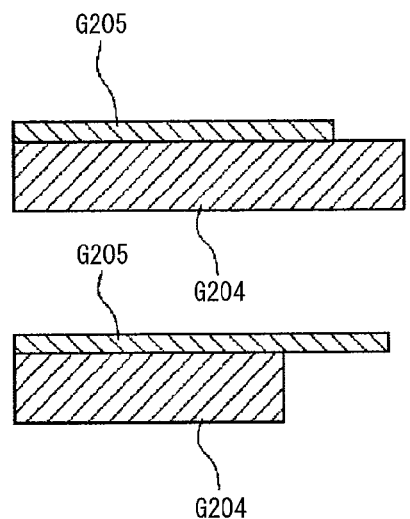
FIG. 25A is an example for displaying graphic information according to another embodiment.

Further, a single graph showing an estimated usage amount of a reagent may be provided to each measurement item. FIG. 25A is a schematic diagram showing an example of displaying graphic information according to another embodiment. In the embodiment shown in FIG. 25A, only one bar G205, which is a graph indicating an estimated usage amount of a reagent, is provided. Moreover, the bar G205 is thinner than a bar G204, which is a graph indicating a remaining amount of the reagent. Moreover, the bar G204 and the bar G205 are arranged, adjacent to each other and parallel to each other. Even in this configuration, it is possible to make the bar G204 indicating a remaining amount of a reagent more conspicuous than the bar G205 indicating an estimated usage amount of the reagent. Further, in this embodiment, a graph indicating a shortage amount of the reagent is not provided. Even if a graph indicating a shortage amount of the reagent is not provided as in this case, when the estimated usage amount of the reagent exceeds the remaining amount of the reagent, the bar G205 extends longer than the bar G204, and the length by which the bar G205 projects rightward from the bar G204 corresponds to the shortage amount of the reagent. Therefore, by confirming the rightward projection amount of the bar G205, the user can discern the shortage amount of the reagent.

Further, in the present embodiment, the width of the bar G105 indicating an estimated usage amount of a reagent is thinner than the width of the bar G104 indicating a remaining amount of the reagent. However, the width of the bar G104 and the width of each bar G105 may be the same. It should be noted that, from a view point of easy discerning of a necessary refill amount of a reagent, it is preferable that the width of the bar G104 is different from the width of each bar G105, and that the width of the bar G104 is greater than that of each bar G105.

Figure 25B:
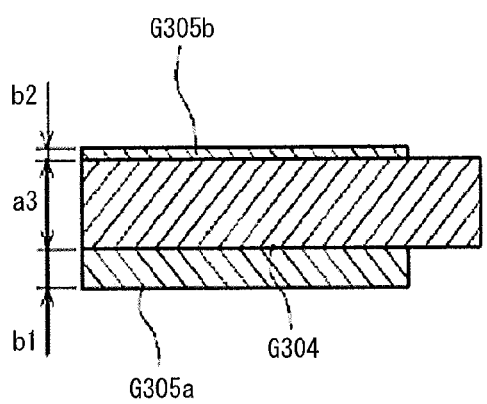
FIG. 25B is an example for displaying graphic information according to another embodiment.

FIG. 25B is a schematic diagram showing an example of displaying graphic information according to another embodiment. In the embodiment shown in FIG. 25B, two bars G305$a$ and G305$b$, each of which is a graph indicating an estimated usage amount of a reagent, are provided so as to sandwich a bar G304 which is a graph indicating a remaining amount of the reagent. The height b2 of the bar G305$b$ is less than the height b1 of the bar G305$a$. Each of the height b1 of the bar G305$a$ and the height b2 of the bar G305$b$ is less than the height a3 of the bar G304. Moreover, the bar G304, the bars G305$a$ and G305$b$ are located, adjacent to each other and in parallel to each other. Even in this configuration, it is possible to make the bar G304 indicating the remaining amount of the reagent more conspicuous than the bars G305$a$ and 305$b$, each indicating the estimated usage amount of the reagent. Moreover, by providing two bars G305$a$ and 305$b$ having different thicknesses from each other, an imaginary line that connects the right ends of the bars 305$a$ and 305$b$ can be imagined, and thus the user can clearly discern the estimated usage amount of the reagent.

Figure 25C:
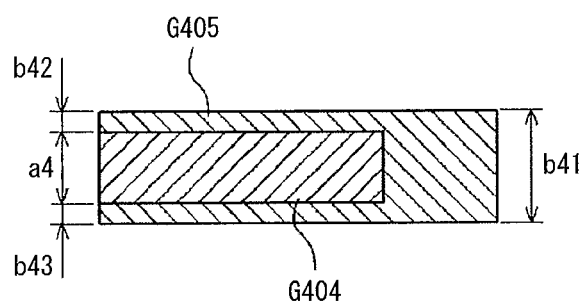
FIG. 25C is an example for displaying graphic information according to another embodiment.

FIG. 25C is a schematic diagram showing an example of displaying graphic information according to still another embodiment. In the embodiment shown in FIG. 25C, a bar G404, which is a graph indicating a remaining amount of a reagent, is provided so as to overlap a single bar G405, which is a graph indicating an estimated usage amount of the reagent. In this embodiment, the height b41 of the bar G405 is greater than the height a4 of the bar G404. Moreover, the bar G405 is arranged so as to project from both ends of upper and lower sides of the bar G404. Accordingly, the overall height including the bar G404 and the bar G405 is not greater than the height b41 of the bar G405. Moreover, the height b42 of a portion of the bar G405 that projects on the upper side of the bar G404 is less than the height a4 of the bar G404. The height b43 of a portion of the bar G405 that projects on the lower side of the bar G404 is also less than the height a4 of the bar G404. The height b42 and the height b43 are identical to each other. Even in this configuration, since the heights of the observable portions of the bar G405 that project from the upper and lower sides of the bar G404, respectively, are less than the height of the bar G404, it is possible to make the bar G404 indicating the remaining amount of the reagent more conspicuous than the bar G405 indicating the estimated usage amount of the reagent. Further, when an estimated usage amount (G405) of a reagent is less than a remaining amount (G404) of the reagent, the bar G405 is shorter than the bar G404. In this case, as in the above embodiment, the bar G405 is viewed as if two graph each indicating the estimated usage amount of the reagent existed on both of the upper and lower sides of the bar G404. Therefore, in this case, an imaginary line that connects the right ends of the two graphs each indicating the estimated usage amount of the reagent can be imagined, and the user can clearly discern the estimated usage amount of the reagent. Further, when an estimated usage amount (G405) of a reagent is greater than a remaining amount (G404) of the reagent, the bar G405 is longer than the bar G404. In this case, as shown in FIG. 25C, the bar G405 projects rightward from the bar G404, by an amount corresponding to the shortage amount of the reagent. Accordingly, by confirming the rightward projection amount of the bar G405, the user can discern the shortage amount of the reagent.

Further, unlike the example of FIG. 25C where the entirety of the bar G404 indicating a remaining amount of a reagent is included, in the height direction, in the bar G405 indicating an estimated usage amount of the reagent, some of the bar G404 indicating the remaining amount of the reagent may be included, in the height direction, in the bar G405 indicating the estimated usage amount of the reagent. Further, even in the configuration where the entirety of the bar G404 indicating a remaining amount of a reagent is included, in the height direction, in the bar G405 indicating an estimated usage amount of the reagent, the height of a portion of the bar G405 projecting from the upper end of the bar G404 indicating the remaining amount of the reagent may be different from the height of a portion of the bar G405 projecting from the lower end of the bar G404 indicating the remaining amount of the reagent.

Figure 25D:
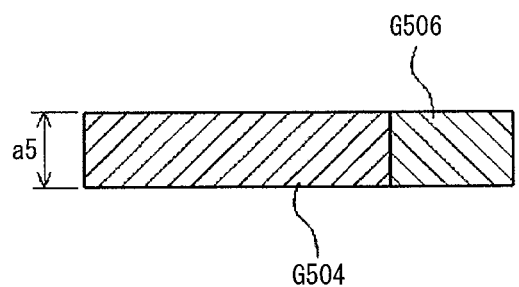
FIG. 25D is an example for displaying graphic information according to another embodiment.

FIG. 25D is a schematic diagram showing an example of displaying graphic information according to still another embodiment. In this embodiment, a graph indicating an estimated usage amount of a reagent is not displayed and a graph indicating a shortage amount of the reagent is displayed. A bar G506, which is a graph indicating a shortage amount of a reagent, is displayed adjacent to the right end of a bar G504, which is a graph indicating the remaining amount of the reagent. That is, the bar G506 is displayed so as to extend rightward from the right end of the bar G504. In this manner, even when the graph indicating the estimated usage amount of the reagent is not displayed, it is possible to show the shortage amount of the reagent, which is more important information, by displaying the bar G506. Moreover, when the bar G506 indicating the shortage amount of the reagent is displayed (that is, when it is estimated that the reagent will run short), the total length of the bar G504 and the bar G506 corresponds to the estimated usage amount of the reagent. Therefore, by confirming the total length of the bar G504 the bar G506, the user can discern the estimated usage amount of the reagent. When the estimated usage amount of the reagent is less than or equal to the remaining amount of the reagent, the bar G504 indicating the remaining amount of the reagent does not necessarily correspond to the estimated usage amount of the reagent, and the user cannot discern the estimated usage amount of the reagent. However, when the remaining amount of the reagent is greater than or equal to the estimated usage amount of the reagent, the possibility that the reagent will run short is low, and thus, the necessity to discern the estimated usage amount of the reagent is low. Therefore, even if the graph indicating the estimated usage amount of the reagent is not displayed, when the graph indicating the shortage amount of the reagent is displayed, the user can discern the shortage amount of the reagent, which is the least amount that should be refilled for performing a sample measurement, and thus, the user can perform the sample measurement without any problem. Moreover, in this embodiment, the height of graphic information corresponds to the height a5 of the bar G504. Therefore, by setting the height of the bar G504 to 90% to 110% of the character height of text information, the display area of the graphic information can be more compact. As a result, it is possible to more efficiently display, in the dimensions of a predetermined display area, information regarding the remaining amount of the reagent (the name of a measurement item, numerical information of a remaining amount of a reagent, graphic information, and numerical information of an excess or shortage amount of the reagent).

Further, in the above, a configuration has been described where the name of a measurement item, numerical information of a remaining amount of a reagent, and numerical information of an excess or shortage amount of the reagent are displayed as text information. However, the present invention is not limited thereto. Either the numerical information of a remaining amount of a reagent or the numerical information of an excess or shortage amount of the reagent may not be displayed, or neither of them may be displayed. Further, numerical information of an estimated usage amount of the reagent may be displayed.

In the above embodiment, a configuration has been described where the bar G104 which is a graph indicating a remaining amount of a reagent and the bar G105 which is a graph indicating an estimated usage amount of the reagent are arranged so as to extend rightward from the same reference position, in parallel to each other. However, the present invention is not limited thereto. As long as the bar G104 and the bar G105 are arranged in parallel to each other and adjacent to each other, each of the bar G104 and the bar G105 may extend rightward, from different reference positions, respectively.

Further, in the present embodiment, a configuration has been described where when the preceding day of the target estimation day is a holiday, an estimated usage amount is calculated by adding a result obtained by multiplying the number of consecutive holidays by an addition component, to an average usage amount of the reagent. However, the present invention is not limited thereto. The rate of increase in a usage amount per holiday is determined, and an average usage amount of the reagent is increased by an amount obtained by multiplying the rate of increase by the number of consecutive holidays, whereby an estimated usage amount may be calculated.

Further, in the embodiment described above, a configuration has been described where when the target estimation day is a holiday, an average usage amount of the reagent is calculated based on usage amounts of the reagent on past holidays, and an estimated usage amount of the reagent is determined based on this average usage amount of the reagent. However, the present invention is not limited thereto. When the target estimation day is a holiday, an estimated usage amount of the reagent on the target estimation day may be determined, based on usage amounts of the reagent on past operation days.

Further, in the embodiment described above, a configuration has been described where by using a usage amount of the reagent on a past day that falls on the same day of the week as the target estimation day, a usage amount of the reagent on the target estimation day is estimated. However, the present invention is not limited thereto. When the target estimation day is an operation day, an average usage amount of the reagent is calculated based on usage amounts of the reagent on past operation days (which may fall on any days of the week), whereby an estimated usage amount can be determined based on this average usage amount of the reagent. Alternatively, when the target estimation day is a non-operation day, an average usage amount of the reagent is calculated based on usage amounts of the reagent on past non-operation days (which may be regular holidays or irregular holidays), whereby an estimated usage amount can be determined based on this average usage amount of the reagent.

Further, in the embodiment described above, a configuration has been described where when the preceding day of the target estimation day is a regular holiday and when the preceding day of the regular holiday is not an irregular holiday, an estimated usage amount of the reagent is calculated without correcting the average usage amount of the reagent. However, the present invention is not limited thereto. When the preceding day of the target estimation day is a regular holiday, an average usage amount of the reagent is corrected in accordance with the number of consecutive regular holidays, whereby an estimated usage amount of the reagent may be calculated. In this case, the number of consecutive non-operation days including irregular holidays and regular holidays immediately before the target estimation day is determined, and an average usage amount of the reagent is corrected in accordance with the number of consecutive non-operation days, whereby an estimated usage amount of the reagent may be calculated.

In the embodiment described above, a configuration where the sample analyzer 1 is an immune analyzer has been described. However, the present invention is not limited thereto. The sample analyzer may be a biochemical analyzer, a blood cell counter, a blood coagulation measuring apparatus, or a sample analyzer other than a blood coagulation measuring apparatus, such as a urine formed element analyzer or a urine qualitative analyzer; and a usage amount of a reagent for the sample analyzer may be estimated by the information processing apparatus 3. Alternatively, a usage amount of a reagent for the sample analyzer 1 may be estimated, by an apparatus (such as a computer) provided separately from the sample analyzer 1.

In the embodiment described above, a configuration has been described where a target estimation day can be designated to a day from the current day to the fifth day from the current day, and usage amounts of reagents for the designated target estimation day are estimated. However, the present invention is not limited thereto. For a day after the fifth day from the current day, usage amounts of reagent may be estimated.

Further, in the embodiment described above, the operation day table OPT is stored in the hard disk 404, separately from the reagent usage history database DB200. However, information of the reagent usage history database DB200 and information of the operation day table OPT may be stored in one database. For example, a field for storing a usage amount of a reagent and a field for storing data indicating whether the day is a non-business day may be provided in the reagent usage history database DB200.

Further, in the embodiment described above, the reagent usage history database DB200 and the operation day table OPT are stored in the hard disk 404 provided in the sample analyzer 1. However, the reagent usage history database DB200 and the operation day table OPT are stored in an external storage device of the sample analyzer 1. Then, when the maintenance status confirmation screen shown in FIG. 23 is to be displayed, the sample analyzer may receive data of the reagent usage history database DB200 and the operation day table OPT from the external storage device and store the data in the RAM 403, and may perform estimation regarding reagents using the data stored in the RAM 403. Further, the sample analyzer 1 may receive, from the external storage device, only data necessary for calculation of usage amounts of reagents for the target estimation day, and may perform estimation regarding reagents using the received data. For example, when the maintenance status confirmation screen shown in FIG. 23 is to be displayed, the sample analyzer 1 receives, from the external storage device, only data necessary for estimation of usage amounts of reagents for the day, and performs calculation, and every time the user changes the date of the target estimation day by operating the date designation icon B200, the sample analyzer 1 may newly receive data necessary for the calculation from the external storage device.

What is claimed is:

1. A sample analyzer comprising:
a measurement unit that holds a reagent to be used in a sample measurement and configured to measure a sample by using the reagent;
a memory that stores a usage amount of the reagent which was used by the measurement unit;
a controller programmed to calculate an estimated usage amount of the reagent for a specific day, based on the usage amount of the reagent stored in the memory; and
a display unit, wherein
the controller operates to control the display unit to display a screen image including:
a first bar graph indicating a remaining amount of the reagent held by the measurement unit;
a second bar graph indicating the estimated usage amount of the reagent for the specific day;
first numerical information indicating, by means of a numerical value, the remaining amount of the reagent; and
second numerical information indicating, by means of a numerical value, an excess or shortage amount of the remaining amount of the reagent relative to the estimated usage amount of the reagent;
wherein the specific day is set as a target estimation day of the week, and the controller is further programmed to calculate the estimated usage amount of the reagent for the specific day by:
filtering the usage amount of the reagent into first usage data relevant to operation days;
filtering the usage amount of the reagent into second usage data relevant to the same day of the week on which the target estimation day of the week falls;
determining an average usage amount of the reagent on the target estimation day of the week based on the first usage data and the second usage data;
determining a number of irregular holidays that are before and consecutive to the target estimation day, where the irregular holidays comprise holidays that do not fall on Saturday or Sunday;
adjusting the average usage amount of the reagent based on the number of irregular holiday; and
determining the estimated usage amount of the reagent for the specific day.

2. The sample analyzer of claim 1, wherein the first bar graph comprises a chart extending in a horizontal the first direction in accordance with a magnitude of the remaining amount of the reagent and the second bar graph comprises a chart extending in the first direction in accordance with a magnitude of the estimated usage amount of the reagent, and to show the first numerical information, the second numerical information, and the graphic information are arranged in a line with the first direction, the first direction being a horizontal direction.

3. The sample analyzer of claim 2, wherein
the controller is further programmed to control the display unit to show the graphic information so as to be sandwiched by the first numerical information and the second numerical information.

4. The sample analyzer of claim 2, wherein
the measurement unit holds a plurality of reagents for a plurality of measurement items, and
the controller further operates to control the display unit to display, for each measurement item, the graphic information, the first numerical information, and the second numerical information, along with a name of the measurement item.

5. The sample analyzer of claim 2, wherein
the controller further operates to control the display unit to display the graphic information within an area having a height which is greater than or equal to a height of a character used for indicating the first numerical information and the second numerical information, and which is less than or equal to twice of the height of the character.

6. The sample analyzer of claim 1, wherein the first numerical information is information indicating, as the remaining amount of the reagent, a number of times of sample measurements performable using the reagent, and the second numerical information is information indicating, as the remaining amount of the reagent, an estimated number of times of sample measurements to be performed using the reagent.

7. The sample analyzer of claim 1, further comprising an input unit, wherein
the controller controls the display unit to display the screen image as a screen image that is manually operable via the input unit for the first time after the measurement unit is powered on.

8. The sample analyzer of claim 1, further comprising an input unit, wherein
the controller controls the display unit to show the screen image as a screen image that is manually operable via the input unit for the first time after a user is logged on the sample analyzer.

9. The sample analyzer of claim 1, wherein the screen image shows displays information indicating a maintenance operation scheduled to be performed on the specific day.

10. The sample analyzer of claim 1, wherein the measurement unit that holds a consumable different from a reagent and measures the sample by using the consumable, and the screen image displays information indicating a remaining amount of the consumable.

11. The sample analyzer of claim 1, wherein
when the specific day is an operation day, the controller is programmed to calculate the estimated usage amount of the reagent for the specific day, by extracting and using a part of the usage amount of the reagent relevant to a past operation day.

12. A non-transitory storage medium having stored therein a computer-executable program executed by at least one processor of a computer system to:
read out a usage amount of a reagent which was used by a measurement unit, from a memory, the memory configured to be a non-transitory storage medium;
calculate an estimated usage amount of the reagent for a specific day, based on the usage amount of the reagent read out from the memory, wherein the specific day is set as a target estimation day of the week, and the controller is further programmed to calculate the estimated usage amount of the reagent for the specific day by;
filtering the usage amount of the reagent into first usage data relevant to operation days;
filtering the usage amount of the reagent into second usage data relevant to the same day of the week on which the target estimation day of the week falls;
determining an average usage amount of the reagent on the target estimation day of the week based on the first usage data and the second usage data;
determining a number of irregular holidays that are before and consecutive to the target estimation day, where the irregular holidays comprise holidays that do not fall on Saturday or Sunday;
adjusting the average usage amount of the reagent based on the number of irregular holiday; and
determining the estimated usage amount of the reagent for the specific day; and
control a display unit to show a screen image including:
a first bar graph indicating a remaining amount of the reagent held by the measurement unit;
a second bar graph indicating the estimated usage amount of the reagent for the specific day;
first numerical information indicating, by means of a numerical value, the remaining amount of the reagent; and
second numerical information indicating, by means of a numerical value, an excess or shortage amount of the remaining amount of the reagent relative to the estimated usage amount of the reagent.

* * * * *